United States Patent
Ma et al.

(10) Patent No.: US 10,752,686 B2
(45) Date of Patent: Aug. 25, 2020

(54) BISPECIFIC ANTIBODY BINDING TO HUMAN CD26 AND HUMAN CD3, PRODUCTION METHOD THEREFOR AND USE THEREOF

(71) Applicants: ZONHON BIOPHARMA INSTITUTE INC., Jiangsu (CN); GENSUN INSTITUTE OF BIOMEDICINE CO., LTD., Jiangsu (CN)

(72) Inventors: Yong Ma, Jiangsu (CN); Peipei Cao, Jiangsu (CN); Anliang Wang, Jiangsu (CN)

(73) Assignees: ZONHON BIOPHARMA INSTITUTE INC., Changzhou (CN); GENSUN INSTITUTE OF BIOMEDICINE CO., LTD., Changzhou (CN)

( * ) Notice: Subject to any disclaimer, the term of this patent is extended or adjusted under 35 U.S.C. 154(b) by 162 days.

(21) Appl. No.: 15/554,476

(22) PCT Filed: Oct. 30, 2015

(86) PCT No.: PCT/CN2015/093383
§ 371 (c)(1),
(2) Date: Aug. 30, 2017

(87) PCT Pub. No.: WO2017/070943
PCT Pub. Date: May 4, 2017

(65) Prior Publication Data
US 2018/0155425 A1    Jun. 7, 2018

(51) Int. Cl.
| A61K 39/395 | (2006.01) |
| C07K 16/30 | (2006.01) |
| C07K 16/28 | (2006.01) |
| C07K 16/46 | (2006.01) |
| A61P 35/00 | (2006.01) |

(52) U.S. Cl.
CPC ........ *C07K 16/2809* (2013.01); *A61K 39/395* (2013.01); *A61P 35/00* (2018.01); *C07K 16/2896* (2013.01); *C07K 16/30* (2013.01); *C07K 16/46* (2013.01); C07K 2317/31 (2013.01); C07K 2317/56 (2013.01); C07K 2317/732 (2013.01); C07K 2317/92 (2013.01)

(58) Field of Classification Search
None
See application file for complete search history.

(56) References Cited

U.S. PATENT DOCUMENTS

| 2009/0136523 | A1* | 5/2009 | Aoyagi | .............. | C07K 16/2896 424/174.1 |
| 2013/0017200 | A1* | 1/2013 | Scheer | ................. | C07K 16/283 424/136.1 |
| 2014/0302037 | A1* | 10/2014 | Borges | .................. | C07K 16/28 424/136.1 |

FOREIGN PATENT DOCUMENTS

| CN | 1867586 A | 11/2006 |
| CN | 101282994 A | 10/2008 |
| CN | 102770456 A | 11/2012 |
| CN | 103641917 A | 3/2014 |
| CN | 104558193 A | 4/2015 |

OTHER PUBLICATIONS

Kearns (Molecular Cancer Therapeutics, vol. 14, No. 7, p. 1625-1636, Apr. 24, 2015) (Year: 2015).*
Rudikoff et al. (Proceedings of the National Academy of Sciences USA, vol. 79, p. 1979-1983, 1982) (Year: 1982).*
Paul, Fundamental Immunology, 3rd Edition, 1993, pp. 292-295 (Year: 1993).*
Bendig M. M. (Methods: A Companion to Methods in Enzymology, 1995; 8:83-93) (Year: 1995).*
Non-English International Search Report and Written Opinion dated Aug. 1, 2016 for Application No. PCT/CN2015/093383 with an English translation.
Office Action dated Apr. 27, 2020, by the National Intellectual Property Administration of the People's Republic of China in corresponding Chinese Patent Application No. 201580008856.6. (4 pages).

\* cited by examiner

*Primary Examiner* — Michael Allen
(74) *Attorney, Agent, or Firm* — Buchanan Ingersoll & Rooney PC

(57) ABSTRACT

Described is a bispecific antibody, and a method for producing the bispecific antibody. The bispecific antibody can be used in the preparation of a drug for treating a tumor with high cell expression of CD26. The antibody specifically binds to human CD26 and human CD3 at the same time.

8 Claims, 9 Drawing Sheets
Specification includes a Sequence Listing.

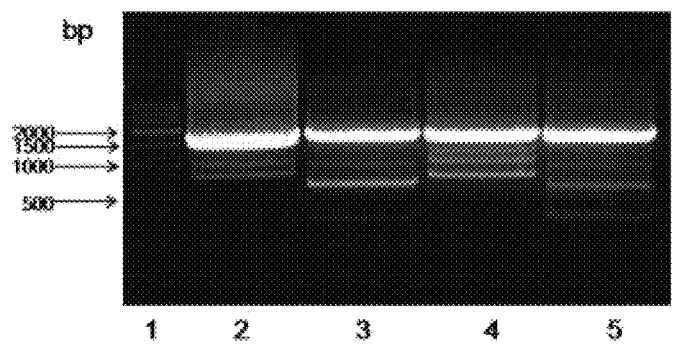
FIG. 1
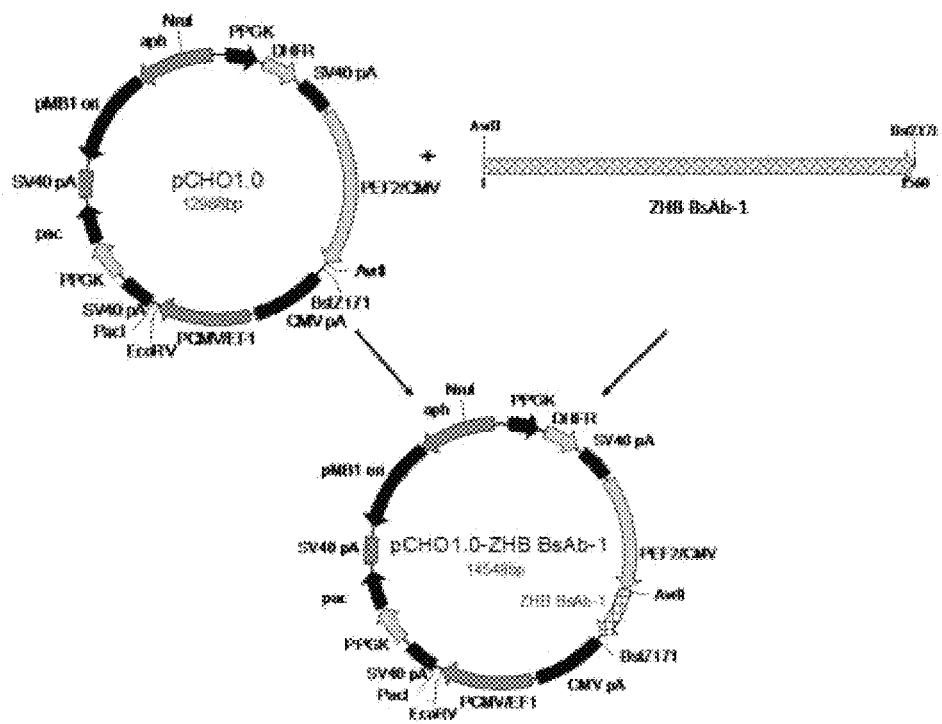
FIG. 2-a

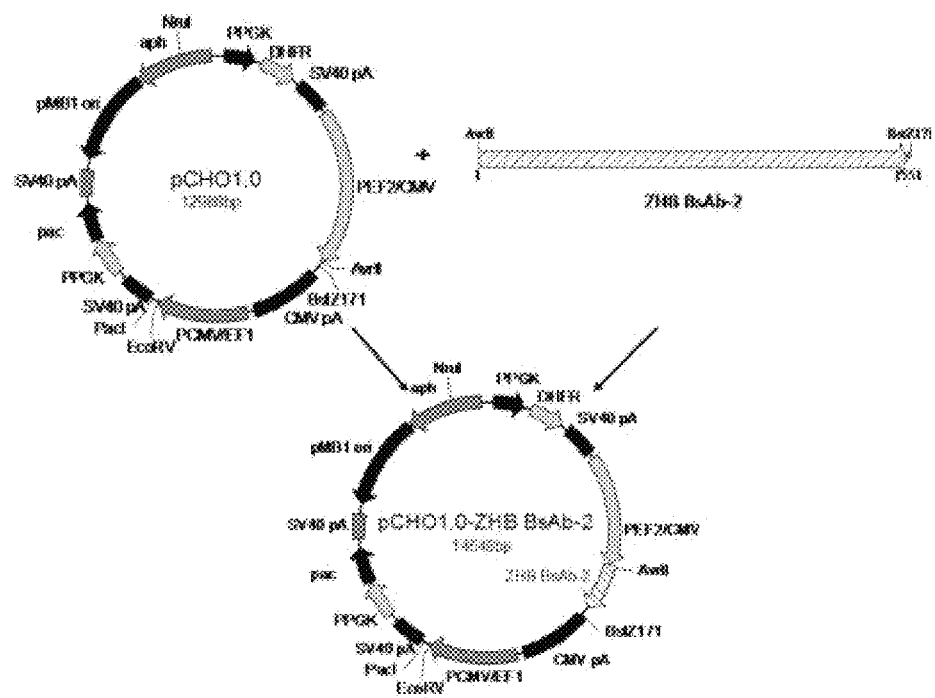
FIG. 2-b
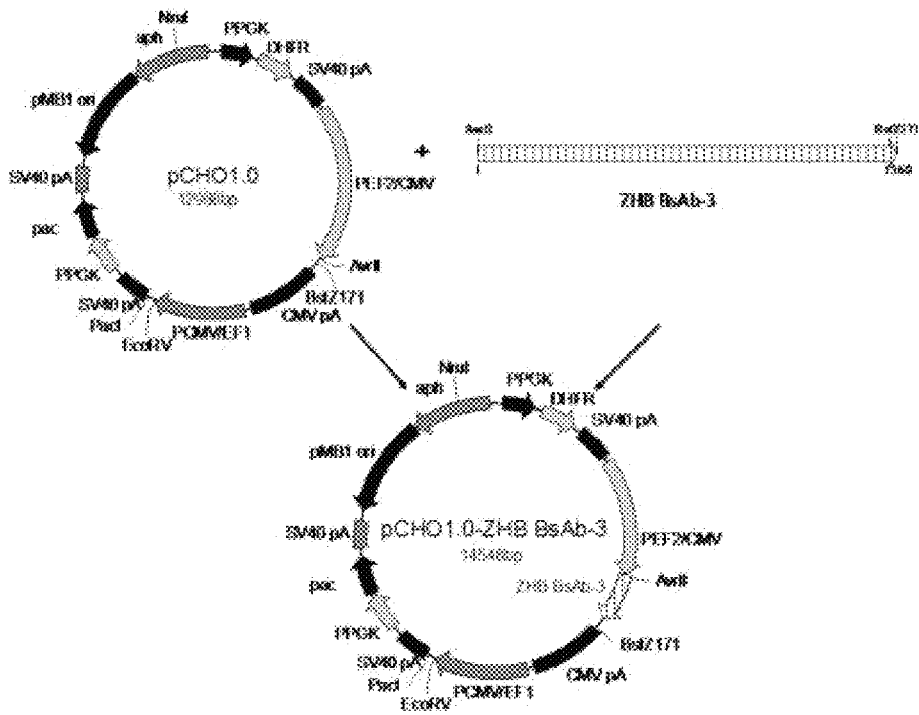
FIG. 2-c

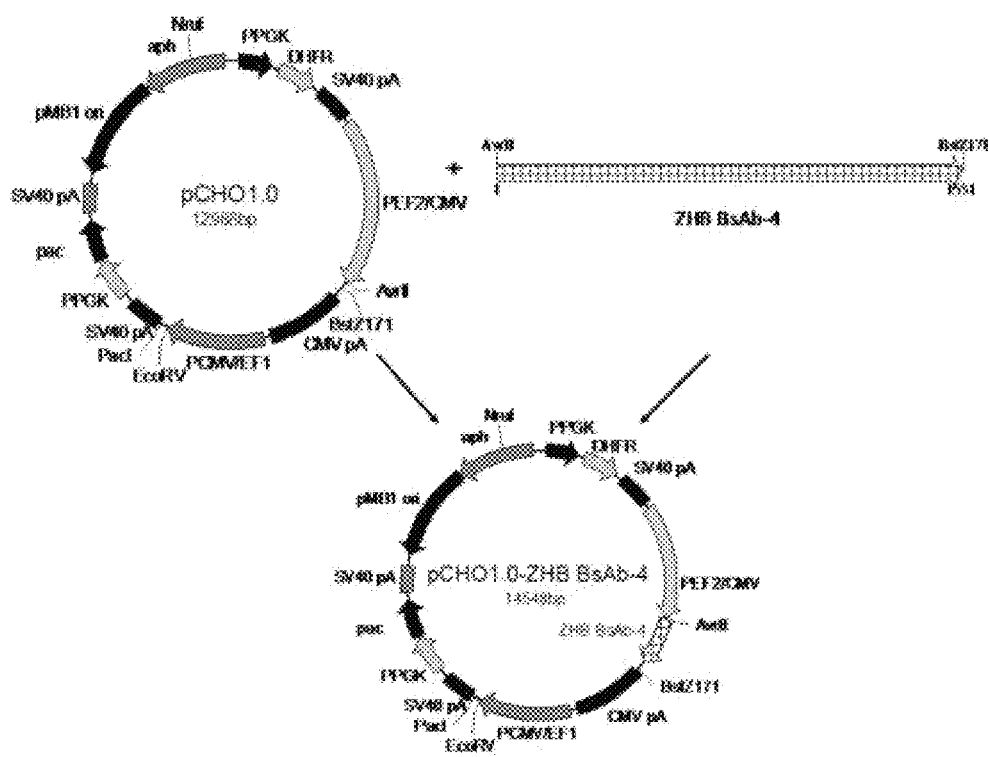
FIG. 2-d
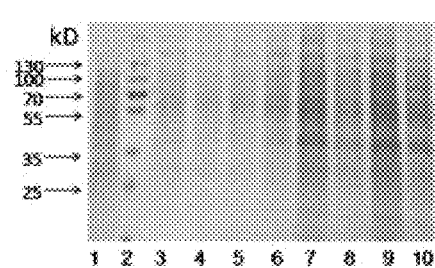
FIG. 3-a
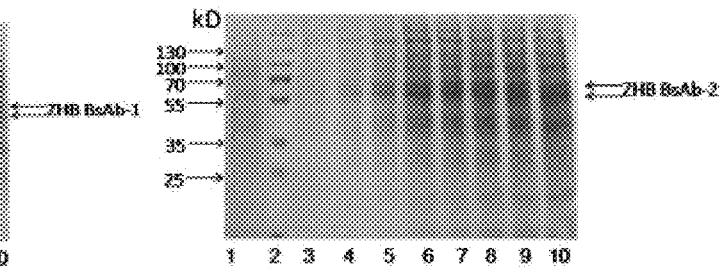
FIG. 3-b
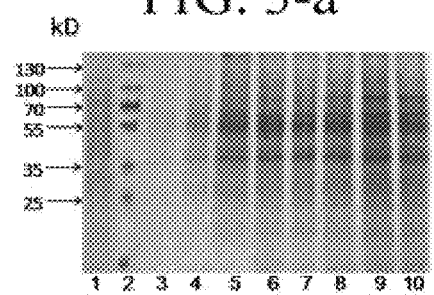
FIG. 3-c
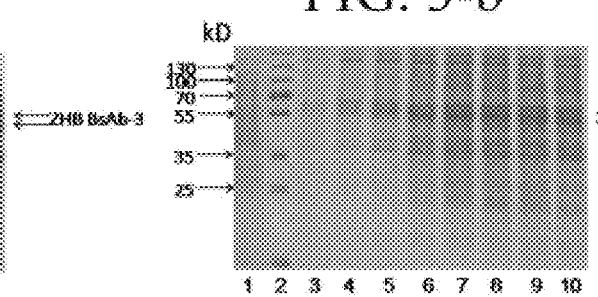
FIG. 3-d

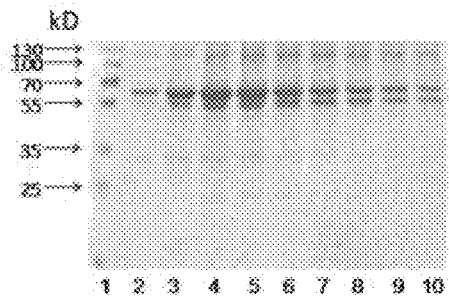
FIG. 4-a
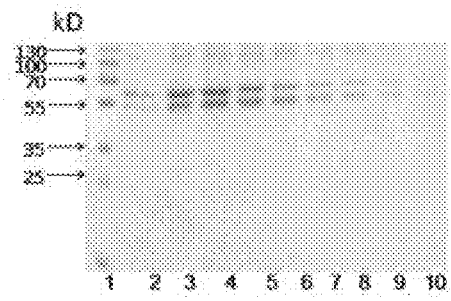
FIG. 4-b
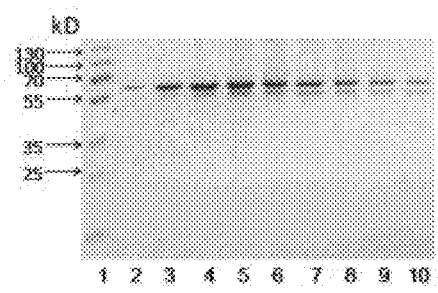
FIG. 4-c
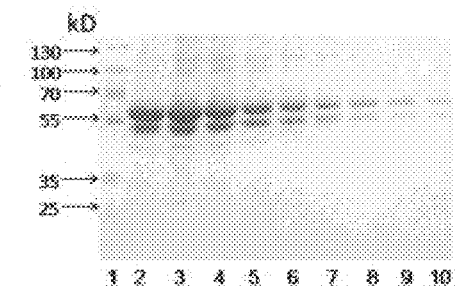
FIG. 4-d
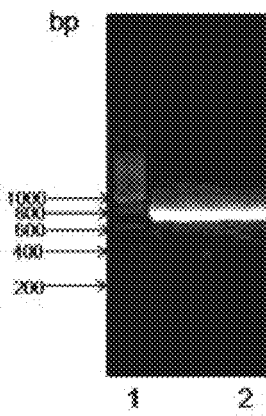
FIG. 5-a
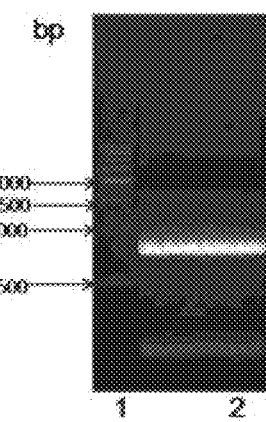
FIG. 5-b

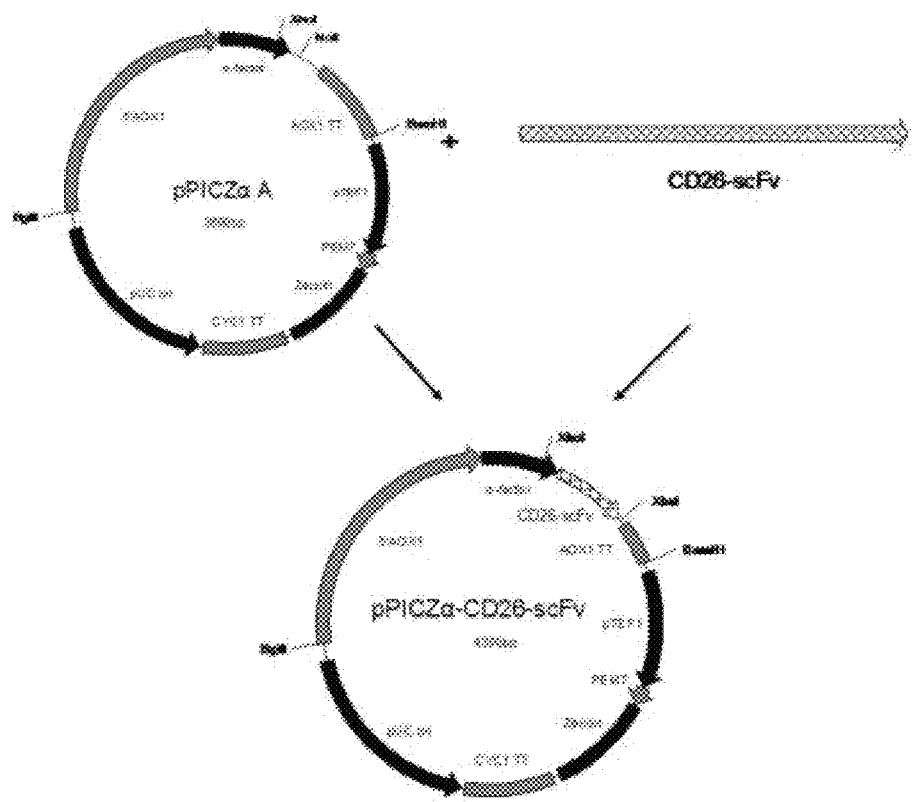
FIG. 6-a
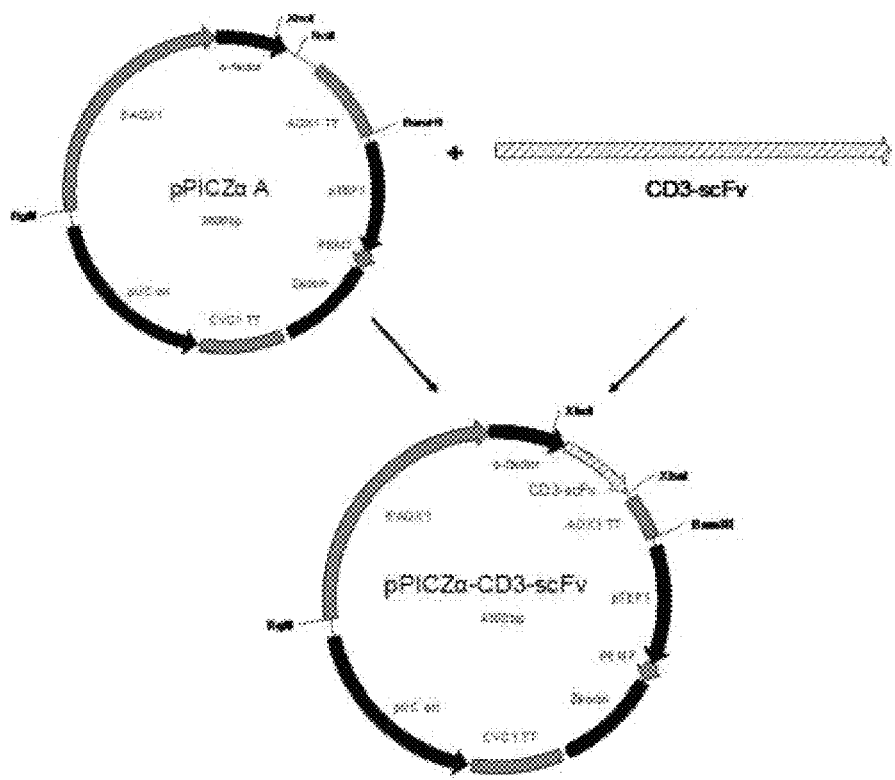
FIG. 6-b

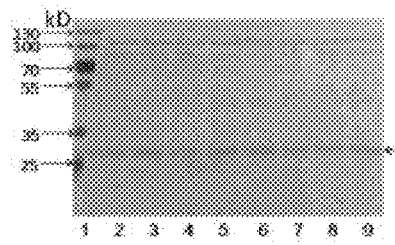
FIG. 7-a
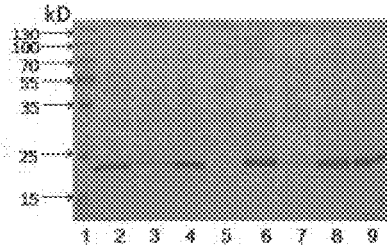
FIG. 7-b
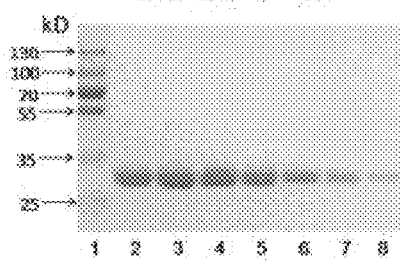
FIG. 8-a
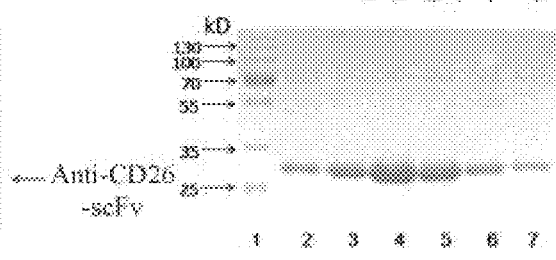
FIG. 8-b
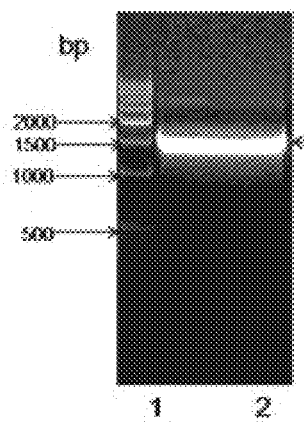
FIG. 9-a
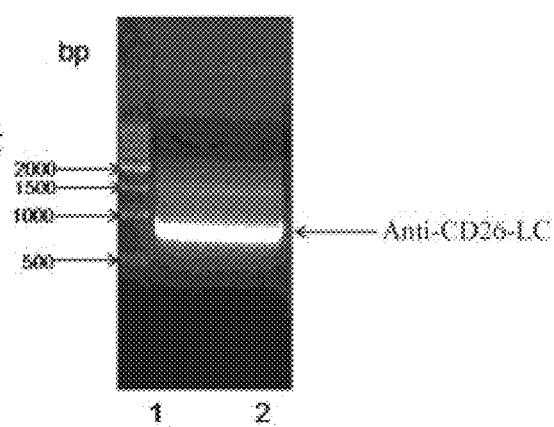
FIG. 9-b

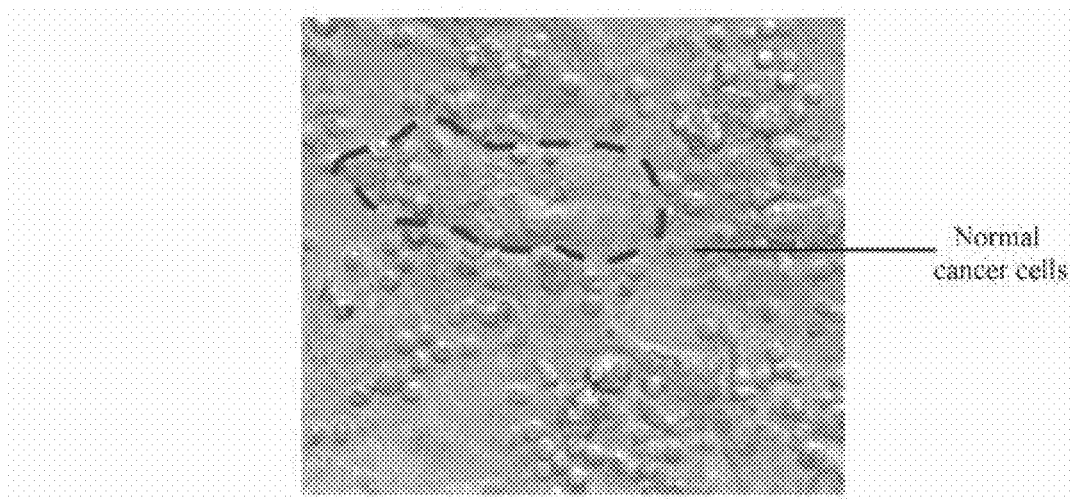
FIG. 15-a
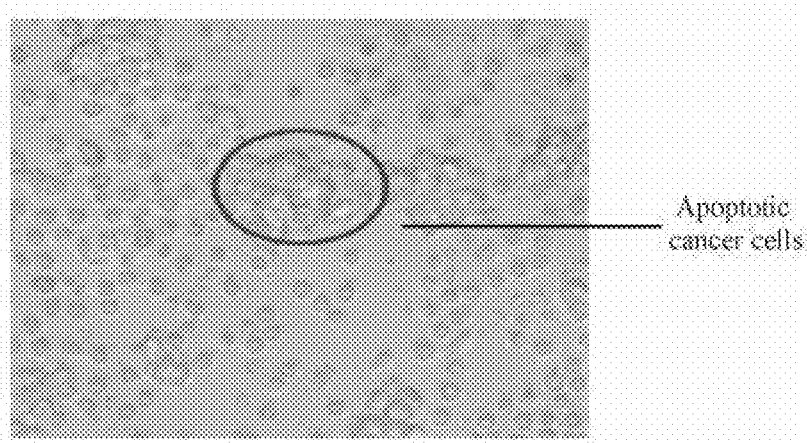
FIG. 15-b
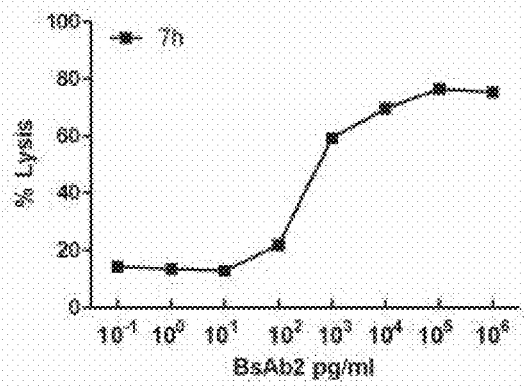
FIG. 16-a
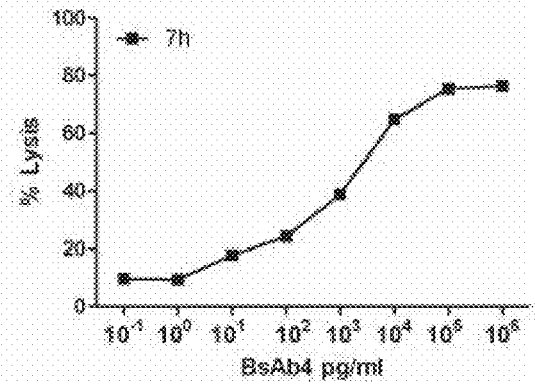
FIG. 16-b

BISPECIFIC ANTIBODY BINDING TO HUMAN CD26 AND HUMAN CD3, PRODUCTION METHOD THEREFOR AND USE THEREOF

RELATED APPLICATION

This application is a national phase entry under 35 USC 371 of International Patent Application No.: PCT/CN2015/093383 filed on 30 Oct. 2015, the content of which is incorporated herein by reference.

FIELD OF THE INVENTION

REFERENCE TO SEQUENCE LISTING SUBMITTED VIA EFS-WEB

This application includes an electronically submitted sequence listing in .txt format. The .txt file cotains a sequence listing entitled "2017-09-21 U 019918-4 ST25.txt" created on Sep. 21, 2017 and is 61,831 bytes in size. The sequence listing contained in this .txt file is part of the specification and is hereby incorporated by reference herein in its entirety.

The present invention relates to a bispecific antibody, and particularly to a single-chain antibody that specifically binds to both human CD26 and human CD3, a production method therefor, and novel use thereof in the preparation of drugs for treating tumors with high expression of CD26 in cells.

DESCRIPTION OF RELATED ART

CD26 is a ubiquitous multifunctional type II transmembrane glycoprotein having a variety of biological functions, which can also be present as a solution in plasma. CD26 often exists in the form of homodimers, a monomer of which contains 766 amino acids and has a relative molecular weight of about 110 kDa. The amino acid residues are divided into five sections from the interior to the exterior, including an intracellular region (1-6), a transmembrane region (7-28), a highly glycosylated region (29-323), a cysteine rich region (324-551) and a C-terminal catalytic domain (552-766). The three-dimensional structure of the CD26 molecules is closely related to its function. The role of CD26 in immunomodulation has been extensively studied. CD26 is a molecular marker of T cell activation and also serves as a costimulatory molecule during T cell signal transduction. It is also involved in a variety of T cell functions including T cell maturation and migration, cytokine secretion, T cell-dependent antibody production, and transformation of B cell immunoglobulin, etc. (Ohnuma et al. (2011) Adv Clin Chem, 53, 51-84).

CD26 can interact with a variety of proteins, such as ADA, CD45, FAP-alpha, and others, and can also bind to ECM, resulting in an increased or decreased infiltration activity of the CD26 expressing cells. Therefore, CD26 plays an important role in tumor biology. The expression level of CD26 on the surface of a variety of neoplastic cells is considerably increased, for example, CD26 is highly expressed in some aggressive T cell malignancies, malignant mesothelioma, nephroma, and some colon cancers (Havre et al. (2008) Front Biosci, 13, 1634-1645). Some CD26[+] colon cancer cell subgroups and CD26[+] malignant mesothelioma cells have obvious tumor stem cell characteristics (Ghani et al. (2011) Biochem Biophys Res Commun, 404, 735-742 and Pang et al. (2010) Cell Stem Cell, 6, 603-615), so CD26 can be used as a molecular marker for a variety of tumors.

At present, human CD26 targeting anti-cancer drugs includes mainly a number of monoclonal antibody drugs, which, however, need to be further improved in terms of their immunogenicities, therapeutic effects, and others. For example, the murine-derived anti-CD26 humanized monoclonal antibody drug YS110 from Y's Therapeutics that has entered the clinical stage can bind specifically to the CD26 epitope on the surface of the target cell, and then the Fc fragment of the IgG of the CD26 binds to the NK cells, macrophages and neutrophils expressing the IgG Fc receptor, thereby exerting a therapeutic effect by means of the ADCC effect of the antibody. However, the Fc receptor may be in an excitatory or an inhibitory form, which affect the effect of the antibody. Moreover, after the humanization of a murine-derived antibody, a murine-derived component still exists, so the HAMA effect can not be eliminated completely. Fucose modification occurs to the Fc fragment of the antibody during expression, which inhibits the ADCC effect. Further, the glycan distribution is complex on the heavy chain, which increases the difficulty in separation, purification and quality control.

Human CD3 is present only on the T cell surface, consists of three different chains including a CD3γ chain, a CD3δ chain, and a CD3ε chain, and often binds to TCR closely to form a TCR-CD3 complex. The CD3 molecule is coupled to the T cell antigen receptor through a salt bridge and thus participates in the T cell signal transduction. CD3 is clustered on the T cells (e.g., by immobilized anti-CD3 antibodies), which may similarly lead to 'T' cell activation caused by T cell receptor binding. The OKT3 antibody used in clinic is a typical representative of anti-CD3 antibodies for the treatment of allograft rejection. The study on bispecific antibodies directing the T cells to attack the cancer cells has been continued for more than 20 years. A large number of differentiated antigens have been developed for the targeted therapy of tumors in the early stages of antibody drugs, most of which are now studied on a new technology platform to construct bispecific antibodies that are coupled with CD3 targeting to improve the therapeutic efficacy, for example CD19, CD33, CEA, EpCAM, HER-2/neu, PSMA or EGF receptor (S. R. Frankel, P. A. Baeuerle (2013) Curr Opin Chem Biol 17, 385-392). Up to now, there is no bispecific antibody structure targeting CD26 and CD3 in combination, and how the order of arrangement of the heavy and light chain variable domains of CD26 and CD3 molecules in the bispecific antibodies affects the biological activity and affinity of the bispecific antibodies for CD26 and CD3 is completely unknown.

SUMMARY OF THE INVENTION

An object of the present invention is to provide a bispecific antibody against CD26 and CD3 having activity of killing tumor cells highly expressing CD26.

The bispecific antibody provided in the present invention comprises a variable domain fragment of an antibody that specifically binds to human CD26 and a variable domain fragment of an antibody that specifically binds to human CD3.

Preferably, in the bispecific antibody, a heavy chain variable domain in the variable domain fragment of the antibody that specifically binds to human CD26 is adjacent to a heavy chain variable domain in the variable domain fragment of the antibody that specifically binds to human CD3, or a light chain variable domain in the variable domain fragment of the antibody that specifically binds to human CD26 is adjacent to a light chain variable domain in the variable domain fragment of the antibody that specifically binds to human CD3.

Preferably, the bispecific antibody has, from an N-terminus to a C-terminus, an arrangement of: light chain variable domain and heavy chain variable domain of the antibody that specifically binds to human CD26, and then heavy chain variable domain and light chain variable domain of the antibody that specifically binds to human CD3, or heavy chain variable domain and light chain variable domain of the antibody that specifically binds to human CD26, and then light chain variable domain and heavy chain variable domain of the antibody that specifically binds to human CD3.

Preferably, the variable domain fragment of the antibody that specifically binds to human CD26 comprises a heavy chain variable domain as shown in SEQ ID NO: 1 and a light chain variable domain as shown in SEQ ID NO: 2; and the variable domain fragment of the antibody that specifically binds to human CD3 comprises a heavy chain variable domain as shown in SEQ ID NO: 4 and a light chain variable domain as shown in SEQ ID NO: 5.

The variable domain of the CD26 antibody is derived from the variable domain gene sequence of the monoclonal antibody YS110 with codon optimization, or from the variable domain of other generally known CD26 antibodies.

The variable domain of the CD3 antibody is derived from a CD3 specific antibody such as OKT-3, TR-66, X35-3, VIT3, CLB-T3/3, CLB-T3.4.2, F111-409, WT31, WT32, CRIS7, F101.01, BMA030(BW264/56), YTH12.5, SPv-T3b, 11D8, XIII-141, XIII-46, XIII-87, 12F6, T3/RW2-8C8, T3/RW2-4136, OKT3D, M-T301, and SMC2, which is known in the art. Preferably, The bispecific antibody according to the present invention has an amino acid sequence as shown in SEQ ID NO: 7, SEQ ID NO: 8, SEQ ID NO: 9, or SEQ ID NO: 10. Preferably, a nucleotide sequence encoding the antibody provided in the present invention is as shown in SEQ ID NO: 20, SEQ ID NO: 21, SEQ ID NO: 22 or SEQ ID NO: 23.

The present invention further provides an expression vector containing the nucleotide sequence, which is preferably pCHO1.0.

The present invention further provides a recombinant host cell comprising the expression vector, which is preferably CHO-S cell.

The present invention further provides a method for producing the antibody, comprising:
Step 1: culturing the recombinant host cell under appropriate conditions, to express the protein of interest; and
Step 2: purifying the protein of interest by chromatography.

The present invention further provides use of the bispecific antibody in the preparation of drugs fur treating tumors with high expression of CD26 in cells.

The present invention further provides use of the bispecific antibody in the preparation of immunotherapeutics for tumor cells mediated by T cells activated with CD3.

Preferably, use of the bispecific antibody in the preparation of drugs for treating renal cancer, prostatic cancer, colon cancer, or mesothelioma is provided.

In the present invention, the anti-CD26×anti-CD3 bispecific antibody is successfully expressed in a eukaryotic cell system,thus being suitable for large-scale production in future. The anti-CD26×anti-CD3 bispecific antibody binds specifically to the CD26 protein with an affinity as high as $10^{-9}$ M, has a potent cytotoxic effect on tumor cell lines highly expressing CD26, and thus can be used in the treatment of solid tumors associated with high CD26 expression. The bispecific antibody mediates the T cells to kill tumor cells highly expressing CD26, and has a better therapeutic effect than a simple anti-CD26 monoclonal antibody; and has the advantages of lower immunogenicity and easier quality control compared with humanized IgG antibodies, due to the absence of Fc fragment, fucose modification, and complex glycan distribution.

BRIEF DESCRIPTION OF THE DRAWINGS

FIG. 1 is an agarose gel electropherogram of a series of ZHB BsAb genes.

Figure 10:
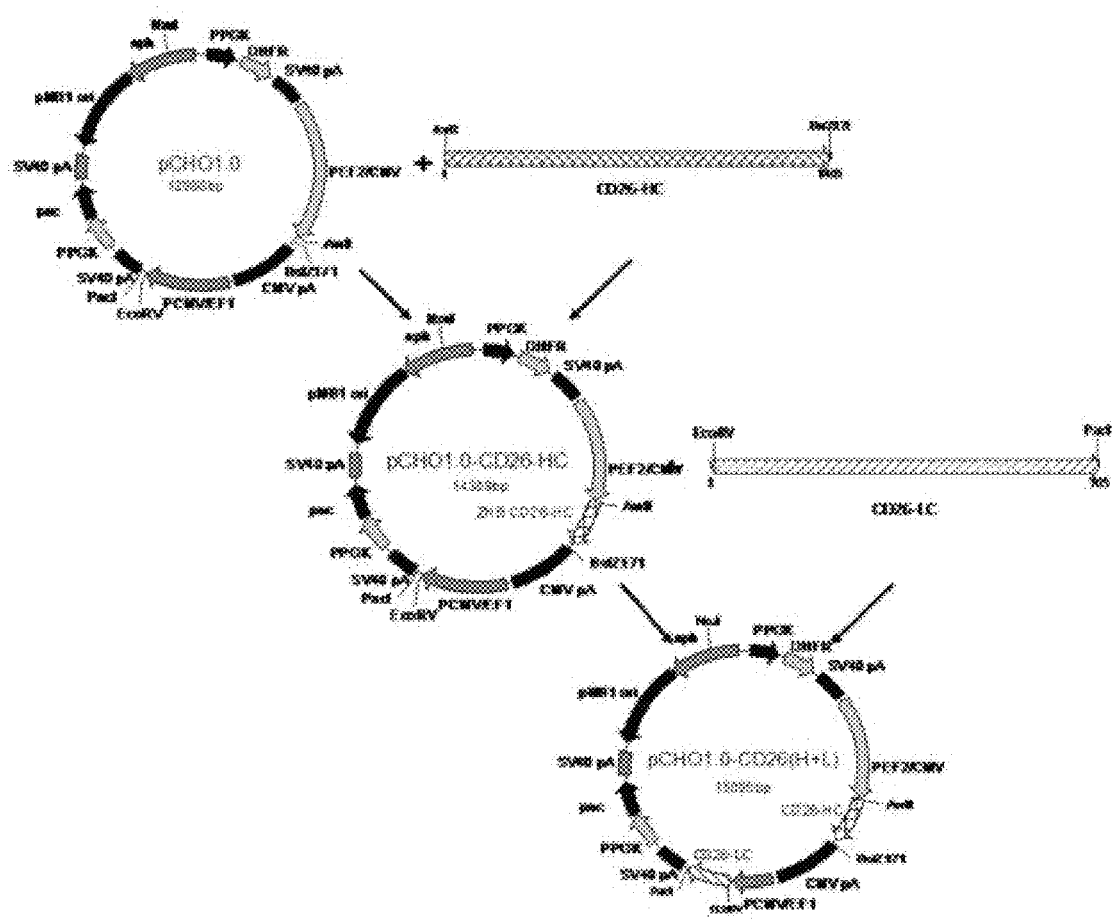

In the figure, Lane 1 is 500 bp DNA Ladder; Lane 2 is a ZHB BsAb-1 gene comprising an AvrII and a BstZ17I cleavage site at two ends, Lane 3 is a ZHB BsAb-2 gene comprising an AvrII and a BstZ17I cleavage site at two ends, Lane 4 is a ZHB BsAb-3 gene comprising an AvrII and a BstZ17I cleavage site at two ends, and Lane 5 is a ZHB BsAb-4 gene comprising an AvrII and a BstZ17I cleavage site at two ends.

FIGS. 2-*a*, 2-*b*, 2-*c*, and 2-*d* show construction processes of plasmids for expressing a series of ZHB BsAb genes.

FIG. 2-*a* shows a process for constructing a ZHB BsAb-1 gene into the expression plasmid pCHO1.0; FIG. 2-*b* shows a process for constructing a ZHB BsAb-2 gene into the expression plasmid pCHO1.0; FIG. 2-*c* shows a process for constructing a ZHB BsAb-3 gene into the expression plasmid pCHO1.0; and FIG. 2-*d* shows a process for constructing a ZHB BsAb-4 gene into the expression plasmid pCHO1.0.

FIGS. 3-*a*, 3-*b*, 3-*c*, and 3-*d* are SDS-PAGE electropherograms showing daily productivity of a series of ZHB BsAbs in a polyclonal cell line of fed-batch culture.

FIG. 3-*a* is an SDS-PAGE electropherogram for identifying the daily productivity of ZHB BsAb-1 in a polyclonal cell line of fed-batch culture, where Lane 1 is a culture supernatant of empty CHO-S cells as a control, Lane 2 is 10-250 KD prestained protein as sample Markers, and Lanes 3-10 shows daily productivity in Days 3-10 of ZHB BsAb-1 in the polyclonal cell line of fed-batch culture, in which the arrows indicate ZHB BsAb-1.

FIG. 3-*b* is an SDS-PAGE electrophoresis for identifying the daily productivity of ZHB BsAb-2 in a polyclonal cell line of fed-batch culture, where Lane 1 is a culture supernatant of empty CHO-S cells as a control, Lane 2 is 10-250 KU prestained protein as sample Markers, and Lanes 3-10 show the daily productivity in Days 3-10 of ZHB BsAb-2 in the polyclonal cell line of fed-batch culture, in which the arrows indicate ZHB BsAb-2.

FIG. 3-*c* is an SDS-PAGE electropherogram for identifying the daily productivity of ZHB BsAb-3 in a polyclonal cell line of fed-batch culture, where Lane 1 is a culture supernatant of empty CHO-S cells as a control, Lane 2 is 10-250 KD prestained protein as sample Markers, and Lanes 3-10 show the daily productivity in Days 3-10 of ZHB BsAb-3 in the polyclonal cell line of fed-batch culture, in which the arrows indicate ZHB BsAb-3.

FIG. 3-*d* is an SDS-PAGE electropherogram for identifying the daily productivity of ZHB BsAb-4 in a polyclonal cell line of fed-batch culture, where Lane 1 is a culture supernatant of empty CHO-S cells as a control, Lane 2 is 10-250 KD prestained protein as sample Markers, and Lanes 3-10 show the daily productivity in Days 3-10 of ZHB BsAb-4 in the polyclonal cell line of fed-batch culture, in which the arrows indicate ZHB BsAb-4.

FIGS. 4-*a*, 4-*b*, 4-*c*, and 4-*d* are SDS-PAGE electropherograms of samples collected after purification by chromatography of culture supernatants of a polyclonal cell line expressing a series of ZHB BsAbs in fed-batch culture.

FIG. 4-a is an SDS-PAGE electropherogram of a sample collected after purification by chromatography of a culture supernatant of a polyclonal cell line expressing ZHB BsAb-1 in fed-batch culture, where Lane 1 is 10-250 KD prestained protein as sample Markers, and Lanes 2-10 are purified samples of ZHB BsAb-1 collected in various collection tubes, in which the arrows indicate ZHB BsAb-1.

FIG. 4-b is an SDS-PAGE electropherogram of a sample collected after purification by chromatography of a culture supernatant of a polyclonal cell line expressing ZHB BsAb-2 in fed-batch culture, where Lane 1 is 10-250 KD prestained protein as sample Markers, and Lanes 2-10 are purified samples of ZHB BsAb-2 collected in various collection tubes, in which the arrows indicate ZHB BsAb-2.

FIG. 4-c is an SDS-PAGE electropherogram of a sample collected after purification by chromatography of a culture supernatant of a polyclonal cell line expressing ZHB BsAb-3 in fed-batch culture, where Lane 1 is 10-250 KD prestained protein as sample Markers, and Lanes 2-10 are purified samples of ZHB BsAb-3 collected in various collection tubes, in which the arrows indicate ZHB BsAb-3.

FIG. 4-d is an SDS-PAGE electropherogram of a sample collected after purification by chromatography of a culture supernatant of a polyclonal cell line expressing ZHB BsAb-4 in fed-batch culture, where Lane 1 is 10-250 KD prestained protein as sample Markers, and Lanes 2-10 are purified samples of ZHB BsAb-4 collected in various collection tubes, in which the arrows indicate ZHB BsAb-4.

FIGS. 5-a and 5-b are agarose gel electropherograms of anti-CD26-scFv and anti-CD3-scFv gene.

FIG. 5-a is an agarose gel electropherogram of anti-CD26-scFv gene, where Lane 1 is 200 bp DNA Ladder; and Lane 2 is an anti-CD26-scFv gene comprising an XhoI and an XbaI cleavage site at two ends.

FIG. 5-b is an agarose gel electropherogram of anti-CD3-scFv gene, where Lane 1 is 500 bp DNA Ladder; and Lane 2 is an anti-CD3-scFv gene comprising an XhoI and an XbaI cleavage site at two ends.

FIGS. 6-a and 6-b show construction processes of plasmids for expressing anti-CD26-scFv and anti-CD3-scFv gene.

FIG. 6-a shows a process for constructing an anti-CD26-scFv gene into the expression plasmid pPICZα; and FIG. 6-b shows a process for constructing an anti-CD3-scFv gene into the expression plasmid pPICZα.

FIGS. 7-a and 7-b show identification of induced expressions of anti-CD26-scFv and anti-CD3-scFv at a low level in a recombinant strain of Pichia pastoris.

FIG. 7-a shows identification of induced expression of anti-CD26-scFv at a low level in a recombinant strain of Pichia pastoris, where Lane 1 is 10-250 KD prestained protein sample Markers, and Lanes 2-9 are culture supernatants of various clones obtained by screening under the antibiotic ZEOCIN stress that are induced with methanol to express anti-CD26-scFv, in which the arrows indicate anti-CD26-scFv.

FIG. 7-b shows identification of induced expression of anti-CD3-scFv at a low level in a recombinant strain of Pichia pastoris, where Lane 1 is 10-250 KD prestained protein sample Markers, and Lanes 2-9 are culture supernatants of various clones obtained by screening under the antibiotic ZEOCIN stress that are induced with methanol to express anti-CD3-scFv, in which the arrows indicate anti-CD3-scFv.

FIGS. 8-a and 8-b are SDS-PAGE electropherograms of samples containing anti-CD26-scFv and anti-CD3-scFv after purification by IMAC.

FIG. 8-a is an SDS-PAGE electropherogram of a sample containing anti-CD26-scFv after purification by IMAC, where Lane 1 is 10-250 KD prestained protein sample Markers, and Lanes 2-8 are purified samples containing anti-CD26-scFv collected in various collection tubes, in which the arrows indicate anti-CD26-scFv.

FIG. 8-b is an SDS-PAGE electropherogram of a sample containing anti-CD3-scFv after purification by IMAC, where Lane 1 is 10-250 KD prestained protein sample Markers, and Lanes 2-7 are purified samples containing anti-CD3-scFv collected in various collection tubes, in which the arrows indicate anti-CD3-scFv.

FIGS. 9-a and 9-b are agarose gel electropherograms of heavy chain and light chain genes of humanized anti-CD26 antibody.

FIG. 9-a is an agarose gel electropherogram of a heavy chain gene of humanized anti-CD26 antibody, where Lane 1 is 500 bp DNA Ladder; and Lane 2 is the heavy chain gene of humanized anti-CD26 antibody comprising an AvrII and a BstZ17I cleavage site at two ends.

FIG. 9-b is an agarose gel electropherogram of a light chain gene of humanized anti-CD26 antibody, where Lane 1 is 500 bp DNA Ladder; and Lane 2 is the light chain gene of humanized anti-CD26 antibody comprising an EcoRV and a PacI cleavage site at two ends.

FIG. 10 shows a process for constructing a plasmid expressing humanized anti-CD26 antibody gene.

Figure 11:
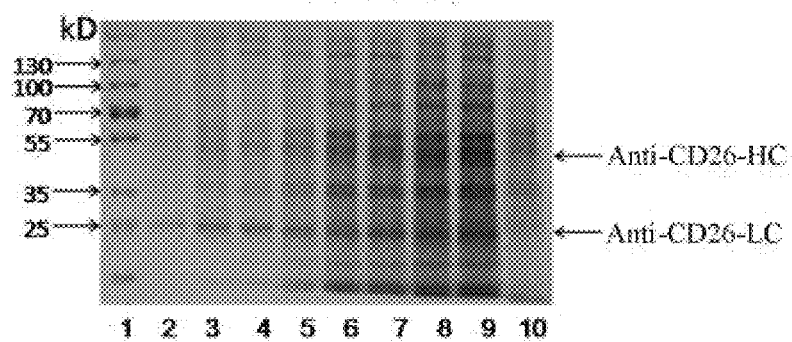

FIG. 11 is a SDS-PAGE electropherogram for identifying daily expression levels of humanized anti-CD26 antibody in a polyclonal cell line cultured in a fed-batch manner.

Lane 1 is 10-250 KD prestained protein sample Markers; Lanes 2-9 show expression levels at Days 2 to 9 of humanized anti-CD26 antibody in the polyclonal cell line in fed-batch culture; and Lane 10 is a supernatant of an empty CHO-S cell culture as a control, where the arrows indicate the heavy chain and the light chain of the humanized anti-CD26 antibody respectively.

Figure 12:
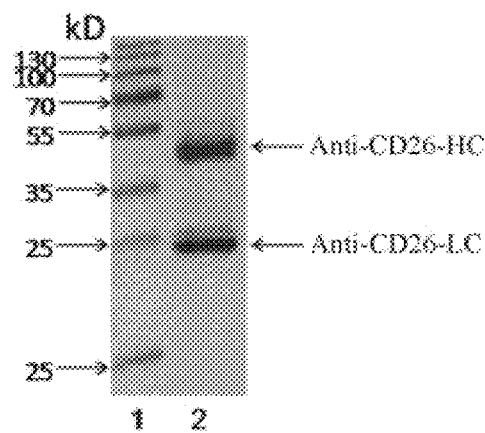

FIG. 12 is an SDS-PAGE electropherogram of a sample collected after purification by prepacked protein A affinity column of a culture supernatant of a polyclonal cell line expressing humanized anti-CD26 antibody in fed-batch culture.

Lane 1 is 10-250 KD prestained protein sample Markers, and Lane 2 is humanized anti-CD26 antibody, where the arrows indicate the heavy chain and the light chain of the humanized anti-CD26 antibody respectively.

Figure 13:
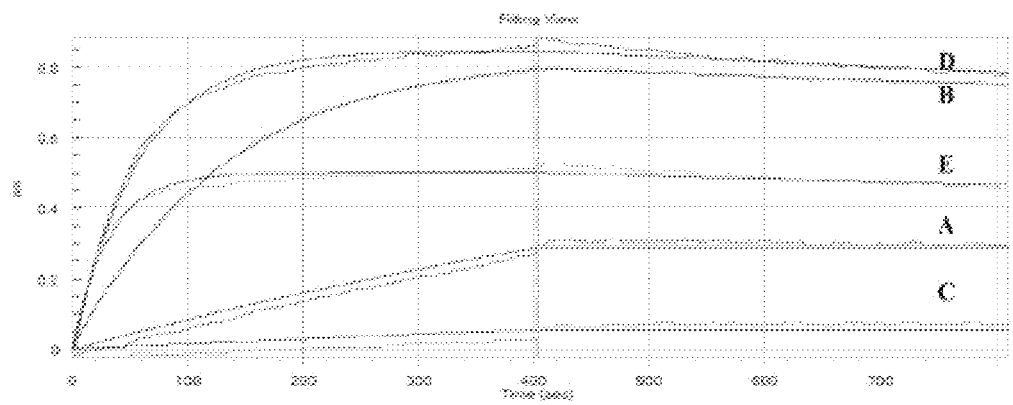

FIG. 13 shows the association and dissociation as the affinity test results, where A is the association and dissociation curves of BsAb1, B is the association and dissociation curve of BsAb4, C is the association and dissociation curves of BsAb3, D is the association and dissociation curves of BsAb2, and E is the association and dissociation curves of anti-CD26 single-chain antibody.

Figure 14:
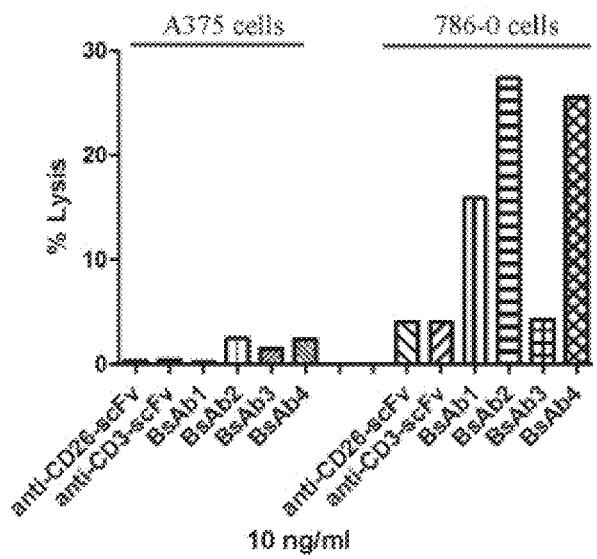

FIG. 14 shows the cytotoxic effect of PBMCs on 786-0 cells and A375 cells mediated by a parent single-chain antibody and bispecific antibodies BsAb1, BsAb2, BsAb3, and BsAb4.

FIG. 15 shows the cytotoxic effect of BsAb4-mediated PBMC cells on 786-0 cells observed under a microscope.

FIG. 15-a shows 786-0 cells in the absence of BsAb4; and FIG. 15-b shows 786-0 cells that are apoptotic in the presence of BsAb4.

FIG. 16 shows the cytotoxic effect of T cells on 786-0 cells mediated by bispecific antibodies BsAb2 and BsAb4.

FIG. 16-a shows the cytotoxic effect of BsAb2-mediated T cells on 786-0 cells; and FIG. 16-b shows the cytotoxic effect of BsAb4-mediated T cells on 786-0 cells.

DETAILED DESCRIPTION OF THE INVENTION

An object of the present invention is to provide a bispecific antibody, which comprises a protein functional domain targeting a first antigen CD26 and a protein functional domain targeting a second antigen CD3. The protein functional domain targeting the first antigen CD26 is operably linked to the protein functional domain targeting the second antigen CD3, while their respective spatial structures are maintained and their respective physiological activities are retained. The protein functional domain targeting the first antigen CD26 and the protein functional domain targeting the second antigen CD3 can be fused together directly without affecting their respective functions. Furthermore, the protein functional domain targeting the second antigen CD3 may be linked to the N terminus or C terminus of the protein functional domain targeting the first antigen CD26 directly or with an additional spacer such as a linker therebetween. Moreover, both the heavy chain variable domain and the light chain variable domain of the protein functional domain targeting the first antigen CD26 may be located at the N terminus of the protein functional domain targeting the first antigen CD26; and both the heavy chain variable domain and the light chain variable domain of the protein functional domain targeting the second antigen CD3 may be located at the N terminus of the protein functional domain targeting the second antigen CD3.

"Bispecific" in the term "bispecific antibody" as used herein refers to specific targeting two different antigens at the same time. In the present invention, the two different antigens are human CD26 and human CD3 respectively.

The term "antibody" as used herein refers to not only intact immunoglobulin, but also a fragment thereof (such as at least an immunologically active segment of the immunoglobulin molecule), for example, Fab, Fab', F(ab')2, Fv fragment, a single-chain antibody molecule, or a multispecific antibody formed from any fragments of an immunoglobulin molecule having one or more CDR domains. The "single-chain antibody" or "scFv" in the present invention refers to an engineered antibody formed by linking a light chain variable domain to a heavy chain variable domain directly or via a short peptide linker.

In certain embodiments, the bispecific antibody consists of anti-CD26-scFv-anti-CD3-scFv, or consists of anti-CD3-scFv-anti-CD26-scFv, or consists of anti-CD26IgG-short peptide linker-anti-CD3-scFv, or consists of anti-CD3-scFv-short peptide linker-anti-CD26IgG.

In an embodiment, the present invention is directed to a method for preventing or treating diseases caused by high CD26 expression with the bispecific antibody, comprising administering a therapeutically effective amount of the bispecific antibody or a pharmaceutical composition. In certain embodiments, the tumors treated are selected from aggressive T cell malignancies, malignant mesothelioma, nephroma, and colon cancers.

The present invention will now be further described through the following non-limiting examples. It should be understood by those skilled in the art that many modifications may be made to the present invention without departing from the spirit of the present invention, and such modifications are within the scope of the present invention. The following experimental methods, unless otherwise specified, are conventional methods and the experimental materials used are readily available from commercial companies, unless otherwise specified.

EXAMPLE 1

Sequence Design of anti-CD26×Anti-CD3 Bispecific Antibody

The heavy chain variable domain (as shown in SEQ ID NO. 1) and the light chain variable domain (as shown in SEQ ID NO. 2) targeting a first antigen CD26 were fused with a short peptide linker (as shown in SEQ ID NO. 3), to form a protein functional domain against CD26. A heavy chain variable region (as shown in SEQ ID NO. 4) and a light chain variable region (as shown in SEQ ID NO. 5) targeting a second antigen CD3 were fused with a short peptide linker (as shown in SEQ ID NO. 6), to form a protein functional domain against CD3. In the protein functional domain targeting the first antigen CD26 and the protein functional domain targeting the second antigen CD3, the heavy chain variable regions and the light chain variable regions were linked in different orders, to form four bispecific antibodies, which were designated as ZHB BsAb-1 (as shown in SEQ ID NO. 7), ZHB BsAb-2 (as shown in SEQ ID NO. 8), ZHB BsAb-3 (as shown in SEQ ID NO. 9), and ZHB BsAb-4 (as shown in SEQ ID NO. 10). For ZHB BsAb-1, a sandfly yellow-related protein (as shown in SEQ ID NO. 11) was used as a signal peptide for secretory expression. For ZHB BsAb-2, a silkworm fibroin-related protein (as shown in SEQ ID NO. 12) was used as a signal peptide for secretory expression. For ZHB BsAb-3, a *Cypridina noctiluca*-related protein (as shown in SEQ ID NO. 13) was used as a signal peptide for secretory expression. For ZHB BsAb-4, a pinemoth-related protein (as shown in SEQ ID NO. 14) was used as a signal peptide for secretory expression. A ZHB BsAb-1 gene (as shown in SEQ ID NO. 16), a ZHB BsAb-2 gene (as shown in SEQ ID NO. 17), a ZHB BsAb-3 gene (as shown in SEQ ID NO. 18), and a ZHB BsAb-4 gene (as shown in SEQ ID NO. 19) before optimization were obtained. The four genes were optimized according to the codon preference for the mammalian cell CHO, to obtain optimized ZHB BsAb-1 (as shown in SEQ ID NO. 20), ZHB BsAb-2 (as shown in SEQ ID NO. 21), ZHB BsAb-3 (as shown in SEQ ID NO. 22), and ZHB BsAb-4 (as shown in SEQ ID NO. 23) respectively. The parameters of the four fusion proteins before and after codon optimization were explained below through comparison.

1) Codon Adaptation Index (CAI)

Generally, when CAI=1, it is considered that a gene is in a most ideal and efficient expression state in an expression system. The expression level of the gene in the host becomes worse with decreasing CAI index. The CAIs of the ZHB BsAb-1, ZHB BsAb-2, ZHB BsAb-3, and ZHB BsAb-4 genes in the CHO are calculated to be 0.68, 0.68, 0.68, and 0.68 respectively before codon optimization. After codon optimization, the CAIs of the optimized ZHB BsAb-1, ZHB BsAb-2, ZHB BsAb-3, and ZHB BsAb-4 genes in the CHO expression system are calculated to be 0.86, 0.86, 0.87, and 0.87 respectively. It can be seen that the expression level of the ZHB BsAb-1, BsAb-2, ZHB BsAb-3, and ZHB BsAb-4 genes in the CHO expression system can be increased through codon optimization of the gene sequences.

2) Frequency of Optimal Codon (FOP)

It can be known through calculation that before codon optimization based on the CHO expression system, the percentage of occurrence of low-usage codons (the codons with a usage of lower than 40%) of the ZHB BsAb-1, ZHB BsAb-2, ZHB BsAb-3 and ZHB BsAb-4 gene sequences is 15%, 17%, 17%, and 16% respectively. In the four genes before optimization, tandem rare codons are used, resulting in reduced translation efficiency and dissolution of translation assemblies. After codon optimization, the occurrence frequency of the low-usage codons of the ZHB BsAb-1, ZHB BsAb-2, BsAb-3, and ZHB BsAb-4 genes in CHO expression system is 0.

3) GC Content

The GC content is ideally distributed in a domain ranging from 30% to 70%, and any peak occurring outside the domain will affect the transcription and translation efficiency to varying degrees. The average GC content in the ZHB BsAb-1, ZHB BsAb-2, ZHB BsAb-3, and ZHB BsAb-4 genes before optimization is 51.83%, 51.90%, 51.89%, and 51.87% respectively. After optimization, the GC content occurring outside the domain from 30% to 70% is removed, and the average GC content in the finally optimized ZHB BsAb-1, ZHB BsAb-2, ZHB BsAb-3, and ZHB BsAb-4 genes is 54.15%, 54.41%, 54.75%, and 54.54% respectively.

EXAMPLE 2

Construction of Expression Vectors, Stable Expression, and Purification of Anti-CD26×Anti-CD3 Bispecific Antibodies 1. Construction of Expression Vectors of Anti-CD26×Anti-CD3 Bispecific Antibodies An AvrII restriction endonuclease cleavage site (as shown in SEQ ID NO. 24) and a kozak sequence (as shown in SEQ ID NO. 25) were introduced upstream and a BstZ17I restriction endonuclease cleavage site (as shown in SEQ ID NO. 26) was introduced downstream of the optimized ZHB BsAb-1 (as shown in SEQ ID NO. 20), ZHB BsAb-2 (as shown in SEQ ID NO. 21), ZHB BsAb-3 (as shown in SEQ ID NO. 22), and ZHB BsAb-4 (as shown in SEQ ID NO. 23). The synthesized fragments were constructed into the pUC57 plasmids (available from GenScript (Nanjing) Co., Ltd), to obtain plasmids for long-term preservation, which were designated as pUC57-ZHB BsAb-1, pUC57-ZHB BsAb-2, pUC57-ZHB BsAb-3, and pUC57-ZHB BsAb-4 plasmid respectively.

The genes of interest were amplified by using the M13F (as shown in SEQ ID NO. 27) and M13R (as shown in SEQ ID NO. 28) as primers and the plasmids as templates. The PCR products were separated by 1% agarose gel electrophoresis (as shown in FIG. 1). The separated PCR products and the pCHO1.0 vector (available from Invitrogen) were digested with AvrII and BstZ17I restriction endonuclease. The insert DNA was ligated to the pCHO1.0 vector backbone by the T4 DNA ligase, transformed into Top10 competent cells, plated in a Kanamycin-resistant LB plates, and incubated overnight at 37° C. Next Day, Screening the positive clones, then sequencing, and aligning. As expected, vectors expressing different forms of anti-CD26-scFv with anti-CD3-scFv fusion proteins were obtained, which were designated as pCHO1.0-ZHB BsAb-1, pCHO1.0-ZHB BsAb-2, pCHO1.0-ZHB BsAb-3, and pCHO1.0-ZHB BsAb-4 respectively (the construction processes of the vectors are as shown in FIGS. 2-a, 2-b, 2-c, and 2-d).

2. Transfection and Expression of Different Anti-CD26× Anti-CD3 Bispecific Antibody The pCHO1.0-ZHB BsAb-1, pCHO1.0-ZHB BsAb-2, pCHO1.0-ZHB BsAb-3, and pCHO1.0-ZHB BsAb-4 vectors were linearized by NruI (R01925, available from NEB), digested overnight, electratransfected into CHO-S cells, and screened with puromycin and MTX together. After one week, the viable cells were calculated. When the viable cells were more than 30%, the cells were transferred to a CO2 shaker, continuously selected in suspension, and incubated at 37° C., 8% CO2, and 130 rpm. The cells were continuously selected by increasing the puromycin and MTX concentrations, until the four fusion proteins were highly expressed. FIG. 3-a, 3-b, 3-c, and 3-d show the daily productivity of ZHB BsAb-1, ZHB BsAb-2, BsAb-3, and ZHB BsAb-4 cells which were glucose Fed-batch cultured.

3. Fed-Batch Culture of anti-CD26×Anti-CD3 Bispecific Antibodies Stable Cells and Purification of Anti-CD26× Anti-CD3 Bispecific Antibodies The stable cells obtained in Step 2 were Fed-batch cultured, to obtain a culture supernatant containing ZHB BsAb-1, ZHB BsAb-2, ZHB BsAb-3, or ZHB BsAb-4, which was collected by low-temperature centrifugation for 15 min at 12000 rpm, and then filtered through a 0.45 μm filter.

The pretreated culture supernatant containing ZHB BsAb-1, ZHB BsAb-2, ZHB BsAb-3, or ZHB BsAb-4 was purified by AKTA avant150 (purchased from GE Healthcare). The purity of ZHB BsAb-1, ZHB BsAb-2, ZHB BsAb-3, and ZHB BsAb-4 proteins was analyzed by SDS-PAGE. The results are shown in FIGS. 4-a, 4-b, 4-c, and 4-d. The Fractions of high purity were combined, and concentrated by ultrafiltration. The buffer was replaced with a PBS buffer, sterilized by filtration, and store at 4° C. for later use.

EXAMPLE 3

Construction, Expression, and Purification of Anti-CD26-scFv and Anti-CD3-scFv

1. Construction of Anti-CD26-scFv and Anti-CD3-scFv Vectors

A heavy chain variable region (as shown in SEQ ID NO. 1) and a light chain variable region (as shown in SEQ ID NO. 2) of an anti-CD26 antibody were directly fused with a polypeptide linker (as shown in SEQ ID NO. 3), to form an anti-CD26-scFv (as shown in SEQ ID NO. 29) proteins. A heavy chain variable region (as shown in SEQ ID NO. 4) and a light chain variable region (as shown in SEQ ID NO. 5) of an anti-CD3 antibody were directly fused with a polypeptide linker (as shown in SEQ ID NO. 6), to form an anti-CD3-scFv (as shown in SEQ ID NO. 30) proteins.

A histidine tag (as shown in SEQ ID NO. 15) was fused respectively to the C terminus of the anti-CD26-scFv and anti-CD3-scFv proteins. An anti-CD26-scFv gene (as shown in SEQ ID NO. 31) before optimization and an anti-CD3-scFv gene (as shown in SEQ ID NO. 32) before optimization were obtained, which were optimized according to the codon preference for *Pichia pastoris,* to obtain an optimized anti-CD26-scFv gene (as shown in SEQ ID NO. 33) and an optimized anti-CD3-scFv gene (as shown in SEQ ID NO. 34). The CAIs of the anti-CD26-scFv and anti-CD3-scFv gene after codon optimization were further calculated to be 0.84 and 0.83 in the *Pichia pastoris* expression system. The percentage of occurrence of low-usage codons of the anti-CD26-scFv and anti-CD3-scFv gene after codon optimization in the *Pichia pastoris* expression system was 0; and the average GC content in the optimized anti-CD26-scFv and anti-CD3-scFv gene was 44.99% and 44.10% respectively.

The restriction endonuclease cleavage site of XhoI (as shown in SEQ ID NO. 35) and XbaI (as shown in SEQ ID NO. 36) were introduced upstream and downstream of the optimized anti-CD26-scFv and anti-CD3-scFv gene respectively, and gene synthesis. The synthesized fragments were constructed into the pUC57 plasmid, to obtain plasmids for long-term preservation, which were designated as pUC57-CD26-scFv and pUC57-CD3-scFv plasmid respectively.

The genes of interest were amplified by using the M13F (as shown in SEQ ID NO. 21) and M13R (as shown in SEQ ID NO. 22) as primers and the plasmids as templates. The PCR product was separated by 1% agarose gel electrophoresis (as shown in FIGS. 5-a and 5-b). The separated PCR product and the pPICZα1 vector (available from Invitrogen) were digested with XhoI and XbaI restriction endonuclease. The cleaved product was ligated to the pPICZα1 backbone vector by the T4 DNA ligase, transformed into Top10 competent cells, plated in a ZEOCIN-containing LB plate, and incubated overnight at 37° C. Next day, screening the positive clones, sequencing, and aligning. As expected, plasmids expressing anti-CD26-scFv and anti-CD3-scFv were obtained, which were designated as pPICZα-CD26-scFv and pPICZα-CD3-scFv respectively (the construction processes of the plasmids are as shown in FIGS. 6-a, and 6-b).

2. Screening of Recombinant Strains Expressing Anti-CD26-scFv and Anti-CD3-scFv Protein Preparation of YPDS solid culture medium: The YPDS solid culture medium was prepared as described in the instruction for EASYSELECT Pichia Expression Kit provided by Invitrogen, which contained 10 g/L of yeast extract, 20 g/L of peptone, 20 g/L of dextrose, 15 g/L of agarose, and 182 g/L of D-sorbitol.

Following the method provided in the instruction for EASYSELECT Pichia Expression Kit, the X-33 strain (C18000, purchased from Invitrogen) was prepared into electrocompetent cells. The pPICZα-CD26-scFv and pPICZα-CD3-scFv plasmid were linearized by SacI restriction endonuclease, and precipitated with ethanol. Then the linearized vector was electrotransfected into X-33 competent cells, plated onto an YPDS solid medium containing 0.5-2.0 mg/mL ZEOCIN (R250-01, purchased from Invitrogen) and incubated at 30° C. for 3-5 days.

3. Induction and Identification of Anti-CD26-scFv and Anti-CD3-scFv Expression in Recombinant Strain Preparation of BMGY culture medium: The BMGY culture medium was prepared as described in the instruction for Multi-Copy Pichia Expression Kit provided by Invitrogen, which contained 10 g/L of yeast extract, 20 g/L of peptone, 3 g/L of $K_2HPO_4$, 11.8 g/L of $KH_2PO_4$, 13.4 g/L of YNB, $4\times10^{-4}$ g/L of biotin, and 10 g/L of glycerol.

Preparation of BMMY culture medium: The BMMY culture medium was prepared as described in the instruction for Multi-Copy Pichia Expression Kit provided by Invitrogen, which contained 10 g/L of yeast extract, 20 g/L of peptone, 3 g/L of $K_2HPO_4$, 11.8 g/L of $KH_2PO_4$, 13.4 g/L of YNB, $4\times10^4$ g/L of biotin, and 5 mL/L of methanol.

The monoclonal strain obtained in Step 2 was picked into 5 mL BMGY medium, and cultured in a 50 mL sterilized centrifuge tube at 30° C., 220 rpm, until $OD_{600}$=2.0-6.0. 1 mL culture was stored as stains, and the remaining culture was centrifugated, re-suspended and then transferred to BMMY for inducing the expression. Methanol was supplemented to give a final concentration of 1% every 24 hours. After a week, the supernatant was collected by centrifugation and analyzed by SDS-PAGE. FIGS. 7-a and 7-b show expressions of anti-CD26-scFv and anti-CD3-scFv in the recombinant strain with optimized codons.

4. Purification of Anti-CD26-scFv and Anti-CD3-scFv Protein

Following the expression method in Step 3, a supernatant containing anti-CD26-scFv or anti-CD3-scFv of the fermentation broth of the recombinant strain with optimized codon were obtained, which was collected by low-temperature centrifugation for 15 min at 12000 rpm, and added with a binding buffer, such that the supernatant finally contained 300 mM NaCl, 20 mM $NaH_2PO_4$, and 10 mM Imidazole. The supernatant was adjusted to pH 7.5 and filtered through a 0.45 μm filter.

By using AKTA avant150 system, the pretreated fermentation containing anti-CD26-scFv or anti-CD3-scFv was purified by affinity chromatography of HISTRAP FF crude column. The binding buffer contained 300 mM NaCl, 20 mM $NaH_2PO_4$, 20 mM Imidazole pH7.5, and the elution buffer contained 300 mM NaCl, 20 mM $Na_2HPO_4$, and 300 mM imidazole, pH7.5. Upon eluting with the elution buffer, the elution peaks were collected and the purity was identified by SDS-PAGE electrophoresis. FIGS. 8-a and 8-b are electropherograms of the anti-CD26-scFv and anti-CD3-scFv fractions. The contents in the collection tubes were combined, concentrated by ultrafiltration, replaced with a PBS buffer, and sterilized by filtration, and preserved at 4° C. for later use.

EXAMPLE 4

Construction, Expression and Purification of Humanized Anti-CD26 Antibody

1. Construction of Heavy and Light Chain of Humanized Anti-CD26 Antibody Vectors A heavy chain variable region (as shown in SEQ ID NO. 1) of an anti-CD26 antibody was directly fused to a human IgG1 heavy chain constant domain, to form a humanized heavy chain of the anti-CD26 antibody (which was designated as anti-CD26-HC herein, as shown in SEQ ID NO. 37). A light chain variable region (as shown in SEQ ID NO. 2) of the anti-CD26 antibody was directly fused to a human IgG1 light chain constant domain, to form a humanized light chain of the anti-CD26 antibody (which was designated as anti-CD26-LC herein, as shown in SEQ ID NO. 38). IgG k (as shown in SEQ ID NO. 39) from *Mus musculus* was used as a signal peptide for secretory expression. An anti-CD26-HC gene sequence (as shown in SEQ ID NO. 40) before optimization and an anti-CD26-LC gene sequence (as shown in SEQ ID NO. 41) before optimization were obtained, which were optimized according to the codon preference for *Cricetulus griseus*, to obtain an optimized anti-CD26-HC gene (as shown in SEQ ID NO. 42) and an optimized anti-CD26-LC gene (as shown in SEQ ID NO. 43). The CAIs of the anti-CD26-HC and anti-CD26-LC gene after codon optimization were further calculated to be 0.86 and 0.86 in the *Cricetulus griseus*. The percentage of occurrence of low-usage codons of the anti-CD26-HC and anti-CD26-LC gene after codon optimization in the *Cricetulus griseus* was 0; and the average GC content in the optimized anti-CD26-HC and anti-CD26-LC gene was 53.89% and 53.10% respectively.

A restriction endonuclease cleavage site of AvrII (as shown in SEQ ID NO. 24) and a kozak sequence (as shown in SEQ ID NO. 25) were introduced upstream, and a restriction endonuclease cleavage site of BstZ17I (as shown in SEQ ID NO. 26) was introduced downstream of the optimized anti-CD26-HC gene, for gene synthesis. The synthesized fragment was constructed into the pUC57 plasmid, to obtain a plasmid for long-term preservation, which was designated as pUC57-CD26-HC plasmid. An EcoRV cleavage site (as shown in SEQ ID NO. 44) and a kozak sequence (as shown in SEQ ID NO. 14) were introduced upstream and a PacI cleavage site (as shown in SEQ ID NO. 45) was introduced downstream of the optimized anti-CD26-LC gene, for gene synthesis. The synthesized fragment was constructed into the pUC57 plasmid, to obtain a plasmid for long-term preservation, which was designated as pUC57-CD26-LC plasmid.

The gene of interest was amplified by using the M13F (as shown in SEQ ID NO. 27) and M13R (as shown in SEQ ID NO. 28) as primers and the pUC57-CD26-HC plasmid as a template. The PCR product was separated by 1% agarose gel electrophoresis (as shown in FIG. 9-$a$). The separated PCR product and the pCHO1.0 plasmid were digested with AvrII and BstZ17I restriction endonuclease. The cleaved product was ligated to the pCHO1.0 vector backbone by the T4 DNA ligase, transformed into Top10 competent cells, plated in a Kanamycin-resistant LB plate, and incubated overnight at 37° C. Next day, Screening the positive clones, sequencing, and aligning. As expected, a plasmid expressing anti-CD26-HC was obtained, which was designated as pCHO1.0-CD26-HC.

The gene of interest was amplified by using the M13F (as shown in SEQ ID NO. 27) and M13R (as shown in SEQ ID NO. 28) as primers and the pUC57-CD26-LC plasmid as a template. The PCR product was separated by 1% agarose gel electrophoresis (as shown in 9-$b$). The separated PCR product and the pCHO1.0-CD26-HC Vector were digested with the EcoRV and PacI restriction endonuclease. The cleaved product was ligated to the pCHO1.0-CD26-HC vector backbone by the T4 DNA ligase, transformed into Top10 competent cells, plated in a Kanamycin-resistant LB plate, and incubated overnight at 37° C. Next Day, Screening the positive clones, sequencing, and aligning. As expected, a plasmid expressing humanized anti-CD26 antibody was obtained, which was designated as pCHO1.0-CD26(H+L) (the construction processes of the plasmid is as shown in FIG. 10).

2. Stable Transfection and Expression of Humanized Anti-CD26 Antibody

The pCHO1.0-CD26(H+L) plasmid was linearized by NruI digested overnight, electrotransfected into CHO-S cells, and selected with puromycin and MTX together. After one week, the viable cell were calculated. When the viable cell were more than 30%, the cells were transferred to a $CO_2$ shaker, continuously selected in suspension, incubated at 37° C., 8% $CO_2$, and 130 rpm. The cells was selected by continuously increasing the puromycin and MTX concentrations, until anti-CD26 antibody was highly expressed. FIG. 11 show the daily productivity of anti-CD26 antibody cells which were glucose Fed-batch cultured.

3. Fed-Batch Culture of Polyclonal Cell Line Expressing Humanized Anti-CD26 Antibody and Purification of Humanized Anti-CD26 Antibody The stable cells obtained in Step 2 through screening under stress were Fed-batch cultured, to obtain a culture supernatant containing humanized anti-CD26 antibody, which was collected by low-temperature centrifugation for 15 min at 12000 rpm 15 min. The buffer was replaced with 20 mM $NaH_2PO4$ in a tangential-flow ultrafiltration system, adjusted to pH=7.0, and then filtered through a 0.45 μm filter.

By using AKTA avant150, the pretreated humanized anti-CD26 antibody was purified on a HiTrap protein A FF column. The binding buffer was 20 mM $NaH_2PO_4$, pH 7.0; and the elution buffer was 20 mM $NaH_2PO_4$, and 0.1 M citric acid, pH 3.0. Upon eluting with the elution buffer, the elution fractions were collected and the purity was identified by SDS-SAGE electrophoresis. The result is as shown in FIG. 12. The fractions of high purity were combined, and concentrated by ultrafiltration. The buffer was replaced with a PBS buffer, sterilized by filtration, and preserved at 4° C. for later use.

EXAMPLE 5

Detection of CD26 Positive Rate on Surfaces of Six Tumor Cell Lines

Test method: Human kidney clear cell adenocarcinoma 786-0 cells (ATCC® CRL-1932), human mesothelioma NCI-H2452 cells (ATCC® CRL-5946), renal cancer Caki-1 cells (ATCC® HTB-46), human colon cancer COLO205 cells (ATCC® CCL-222), human prostatic cancer PC-3 cells (ATCC® CRL-1435), and human malignant melanoma A375 cells (ATCC® CRL-1619) in the logarithmic growth phase were trypsinized. The cells were harvested by centrifugation at 1000 rpm for 5 min, and washed twice with PBS buffer. One portion of $1.0 \times 10^6$ cells was re-suspended in 250 μL PBS buffer, and an anti-CD26 antibody was added to give a final concentration of 10 μg/mL and incubated at room temperature for 1 hr. After incubation, the cells were washed twice with PBS buffer, and then 250 μL of Anti-His-tag-ALEXA FLUOR 488 antibody (MBL, Cat#D291-A48) that was 1:2000 diluted was added and incubated at room temperature for 1 hour. After incubation, the cells were washed thrice with PBS buffer, re-suspended in 300 μl PBS buffer, and detected by flow cytometer (BD, AccuriC6).

Test result: The test result is shown in Table 1.

TABLE 1

| CD26 positive rate on surfaces of various tumor cell lines | | | | | | |
|---|---|---|---|---|---|---|
| Cell line | 786-0 | NCI-H2452 | PC-3 | Caki-1 | COLO205 | A375 |
| CD26 positive rate on cell surfaces | 99.9% | 93.9% | 93.8% | 69.5% | 42.4% | 2.9% |

Conclusions: CD26 are highly expressed on all of 786-0 cells, NCI-H2452 cells, Caki-1 cells, COLO205 cells, and PC-3 cells. A375 cells express substantially no CD26, and can be used as a negative control in this test.

EXAMPLE 6

Detection of CD3 Positive Rate on Surfaces of Jurkat Cells

Test method: Jurkat cells (ATCC® TIB-152) in the logarithmic growth phase were collected by centrifugation at 1000 rpm for 5 min, and washed twice with PBS buffer. One portion of $1.0 \times 10^6$ cells was re-suspended in 250 μL PBS buffer, and an anti-CD3 single-chain antibody was added to give a final concentration of 30 μg/mL and incubated at room temperature for 1 hour. After incubation, the cells were washed twice with PBS buffer, and then 250 μL of Anti-His-tag-ALEXA FLUOR 488 antibody that was 1:2000 diluted was added and incubated at room temperature for 1 hr. After incubation, the cells were washed thrice with PBS buffer, re-suspended in 300 μL PBS, and detected by flow cytometer.

Test result: As shown by FACS analysis, the CD3 positive rate on the surface of Jurkat cells is 46.6%.

Conclusions: CD3 is expressed on the surface of Jurkat cells.

EXAMPLE 7

Detection of Binding Rates of Bispecific Antibodies to Tumor Cells Highly Expressing CD26

Test method: 786-0 and NCI-H2452 cells in the logarithmic growth phase were trypsinized. The cells were harvested by centrifugation at 1000 rpm for 5 min, and washed twice with PBS buffer. One portion of $1.0 \times 10^6$ cells was re-suspended in 250 μL PBS butler, and BsAb1, BsAb2, BsAb3, and BsAb4 were respectively added to give a final concentration of 10 and incubated at room temperature for 1 hr. After incubation, the cells were washed twice with PBS buffer, and then 250 μL of Anti--His-tag-ALEXA FLUOR 488 antibody that was 1:2000 diluted was added and incubated at room temperature for 1 hr. After incubation, the cells were washed thrice with PBS, re-suspended in 300 μL PBS buffer, and detected by flow cytometer.

The test result is shown in Table 2.

TABLE 2

Binding rates of bispecific antibodies to tumor cells highly expressing CD26

| Binding rate | BsAb1 | BsAb2 | BsAb3 | BsAb4 |
|---|---|---|---|---|
| 786-0 cells | 41.1% | 99.6% | 9.4% | 98.0% |
| NCI-H2452 cells | 1.1% | 71.8% | 0.7% | 1.4% |
| PC-3 cells | 1.2% | 42.8% | 0.1% | 62.9% |
| Caki-1 cells | 1.1% | 49.9% | 1.2% | 1.1% |
| COLO205 cells | 0.1% | 14.0% | 0.4% | 0.2% |

Conclusions: All of the bispecific antibodies BsAb1, BsAb2, BsAb3, and BsAb4 can specifically bind to the CD26 molecules on the surfaces of the tumor cells, and particularly BsAb2 and BsAb4 bind to the CD26 molecules on the surfaces of the tumor cells with a quite high rate.

EXAMPLE 8

Detection of Binding Rates of Bispecific Antibodies to Jurkat (CD3+) Cells

Test method: Jurkat cells in the logarithmic growth phase were harvested by centrifugation at 1000 rpm for 5 min, and washed twice with PBS buffer. One portion of $1.0 \times 10^6$ cells was re-suspended in 250 μL PBS buffer, and BsAb1, BsAb2, BsAb3, and BsAb4 were respectively added to give a final concentration of 10 μg/mL and incubated at room temperature for 1 hour. After incubation, the cells were washed twice with PBS, and then 250 μL of Anti-His-tag-ALEXA FLUOR Fluor 488 antibody that was 1:2000 diluted was added and incubated at room temperature for 1 hour. After incubation, the cells were washed thrice with PBS buffer, re-suspended in 300 μL PBS, and detected by flow cytometer.

Test result: As shown by FACS analysis, BsAb1 binds to Jurkat cells at a rate of 0.1%; BsAb2 binds to Jurkat cells at a rate of 92.0%; BsAb3 binds to Jurkat cells at a rate of 0.2%; and BsAb4 binds to Jurkat cells at a rate of 56.5%.

Conclusions: All of the bispecific antibodies BsAb1, BsAb2, BsAb3, and BsAb4 can specifically bind to the CD3 molecules on the surfaces of Jurkat cells, and particularly BsAb2 and BsAb4 bind to the CD3 molecules on the surfaces of Jurkat cells with a quite high rate.

Example 9

Identification of Affinities of Bispecific Antibodies to CD26 Protein

Test method: The affinities of the bispecific antibodies to CD26 protein were detected by using the Molecular Interaction Instrument Fortebio Qke, following the instruction of operation of immersive readable Amine Reactive 2nd Generation Biosensor (Fortebio, AR2G).

Test result: The test result is shown in FIG. 13. The affinity constant is $KD_{(BsAb1)}=9.29 \times 10^{-9} M$; $KD_{(BsAb2)}=3.44 \times 10^{-9} M$; $KD_{(BsAb3)}=1.0 \times 10^{-8} M$; $KD_{(BsAb4)}=1.97 \times 10^{-9} M$; and $KD_{(anti-CD26-scFv)}=1.00 \times 10^{-9} M$.

Conclusions: All of the bispecific antibodies BsAb1, BsAb2, BsAb3, and BsAb4 have an affinity to CD26 protein; and the affinity constant of BsAb2 and BsAb4 to the CD26 protein is close to the affinity constant of the parent single-chain antibody to the CD26 protein.

Example 10

Detection of Cytotoxic Effect of PBMC on 786-0 and A375 Cells Mediated by Bispecific Antibodies and Parent Single-Chain Antibodies Test method: 786-0 cells in the logarithmic growth phase were trypsinized. The cells were harvested by centrifugation at 1000 rpm for 5 min, and washed twice with PBS. One portion of $1.0 \times 10^6$ cells was re-suspended in 1 mL PBS, and a Calcein-AM solution was added to give a final concentration of 2.5 μM. The cells were incubated at 37° C. for 30 min. After incubation, the cells were washed thrice with PBS, and diluted to $6.0 \times 10^5$ in RPMI-1640 medium (GIBCO, Cat #31800022), 50 μL per well was added to a U-shaped 96-well plate, and then 50 μL of a test sample was added. For the blank control group, 50 μL of RPMI-1640 medium was added; for the positive control group, 50 μL, of 3% TRITON-100 was added; and for the test groups, 50 μL of BsAb1 (10 ng/mL), 50 μL of BsAb2 (10 ng/mL), 50 μL of BsAb3 (10 ng/mL), 50 μL of BsAb4 (10 mg/mL), 50 μL of Anti-CD3-scFv (10 ng/mL), and 50 μL of Anti-CD26-scFv (10 ng/mL) were added respectively. The cells were incubated at 37° C. for 30 min. After incubation, PBMC cells were added at a ratio of 786-0: PBMC=1:15, and continuously incubated at 37° C. for 3 hours. After incubation, a suitable amount of cell culture supernatant was removed and detected on a microplate reader at an excitation wavelength of 485 nm and an emission wavelength of 515 nm.

The A375 cells were used as a negative control, and the operations were the same as above.

Test result: The cytotoxic effect of BsAb4-mediated PBMC cells on 786-0 cells was observed under a microscope. FIG. 15-a is a micrograph taken after the 786-0 cells are incubated with the PBMC cells for 3 hours, where the cells delimited by the white dotted line are cancer cells growing normally, and FIG. 15-b is a micrograph taken after the 786-0 cells are incubated with BsAb4 (10 ng/ml) for 30 min, and then incubated with the PBMC cells for 3 hours, where the arrow indicates the position of T cells, and the cells delimited by the white circle are apoptotic cancer cells.

The cytotoxic effect of PBMC on 786-0 and A375 cells mediated by the bispecific antibodies and the parent single-chain antibody is shown in Table 3, and FIG. 14. The bispecific antibody BsAb1 has a lysis rate for 786-0 cells of 15.9% at 10 ng/mL; BsAb2 has a lysis rate for 786-0 cells of 27.4% at 10 ng/mL; BsAb3 has a lysis rate for 786-0 cells of 4.3% at 10 ng/mL; BsAb4 has a lysis rate for 786-0 cells of 25.5% at 10 ng/mL; the single-chain antibody anti-CD26-scFv has a lysis rate for 786-0 cells of 4.1% at 10 ng/mL; and the single-chain antibody anti-CD3-scFv has a lysis rate for 786-0 cells of 4.1% at 10 ng/mL.

The bispecific antibody BsAb1 has a lysis rate for the negative control A375 cells of 0.2% at 10 ng/mL; BsAb2 has a lysis rate for A375 cells of 2.5% at 10 ng/mL; BsAb3 has a lysis rate for A375 cells of 1.5% at 10 ng/mL; BsAb4 has a lysis rate for A375 cells of 2.4% at 10 ng/mL; the single-chain antibody anti-CD26-scFv has a lysis rate for A375 cells of 0.3% at 10 ng/mL; and the single-chain antibody anti-CD3-scFv has a lysis rate for A375 cells of 0.4% at 10 ng/mL.

TABLE 3

Cytotoxic effect of bispecific antibodies and parent single-chain antibodies on 786-0 and A375 cells

| Lysis (%) | BsAb1 | BsAb2 | BsAb3 | BsAb4 | Anti-CD26-scFv | Anti-CD3-scFv |
| --- | --- | --- | --- | --- | --- | --- |
| 786-0 cells | 15.9 | 27.4 | 4.3 | 25.5 | 4.1 | 4.1 |
| A375 cells | 0.2 | 2.5 | 1.5 | 2.4 | 0.3 | 0.4 |

Conclusions: The parent single-chain antibodies anti-CD26-scFv and anti-CD3-scFv, and the bispecific antibodies BsAb1, BsAb2, BsAb3, and BsAb4 have not cytotoxic effect on the negative control A375 cells; and the parent single-chain antibodies anti-CD26-scFv and anti-CD3-scFv, and the bispecific antibodies BsAb1, BsAb2, BsAb3, and BsAb4 have a cytotoxic effect on the 786-0 cells. Moreover, the cytotoxic effects of the bispecific antibodies BsAb1, BsAb2, and BsAb4 on the 786-0 cells are better than that of the parent single-chain antibodies anti-CD26-scFv and anti-CD3-scFv.

EXAMPLE 11

Detection of Cytotoxic Effect of PBMC on 786-0 and A375 Cells Mediated by Humanized Anti-CD26 Antibody Test method: 786-0 cells in the logarithmic growth phase were trypsinized. The cells were harvested by centrifugation at 1000 rpm for 5 min, and washed twice with PBS. $1.0 \times 10^6$ cells were re-suspended in 1 mL PBS, and a Calcein-AM solution was added to give a final concentration of 2.5 µM. The cells were incubated at 37° C. for 30 min. After incubation, the cells were washed thrice with PBS_buffer, and diluted to $6.0 \times 10^5$ in RPMI-1640 medium. 50 µL per well was added to a U-shaped 96-well plate, and then 50 µL of a test sample was added. For the blank control group, 50 µL of RPMI-1640 medium was added; for the positive control group, 50 µL of 3% TRITON-100 was added; for the test groups, 50 µL of various concentrations of humanized anti-CD26 antibody (10 ng/mL, 1 ng/mL and 0.01 ng/mL) were added respectively. The cells were incubated at 37° C. for 30 min. After incubation, PBMC cells were added at a ratio of 786-0: PBMC=1:15, and continuously incubated at 37° C. for 3 hours. After incubation, a suitable amount of cell culture supernatant was removed and detected on a microplate reader at an excitation wavelength of 485 nm and an emission wavelength of 515 nm.

The A375 cells were used as a negative control, and the operations were the same as above. The medium used was DMEM medium (GIBCO, Cat #12800-082).

Test result: The test result is shown in Table 4. The humanized anti-CD26 antibody has a lysis rate for 786-0 cells of 9.6%, 1.5%, and 0.4% at 10 ng/mL, 1 ng/mL, and 0.01 ng/mL respectively; and the humanized anti-CD26 antibody has a lysis rate for A375 cells of 0.2%, 0.1%, and 0.4% at 10 ng/mL, 1 ng/mL, and 0.01 ng/mL respectively.

TABLE 4

Cytotoxic effect of humanized anti-CD26 antibodies on 786-0 and A375 cells

| Lysis rate (%) | 10 ng/mL | 1 ng/mL | 0.01 ng/mL |
| --- | --- | --- | --- |
| YS110 (786-0 cells) | 9.6 | 1.5 | 0.4 |
| YS110 (A375 cells) | 0.2 | 0.1 | 0.4 |

Conclusions: The humanized anti-CD26 antibody has no obvious cytotoxic effect on the negative control A375 cells; in contrast, the humanized anti-CD26 antibody has a concentration-dependent cytotoxic effect on 786-0 cells. However, compared with humanized anti-CD26 antibody, the bispecific antibodies BsAb1, BsAb2, and BsAb4 of the present invention have a greatly increased cytotoxic effect on 786-0 cells.

EXAMPLE 12

Detection of Cytotoxic Effect of T Cells on 786-0 and A375 Cells Mediated by Bispecific Antibodies Test Method:
1. Isolation of T Cells Following the instruction of operations of Lymphocyte Separation Medium (MP, Cat #50494), PBMC cells were isolated from human blood. Following the instruction of operations of Human Erythrocyte Lying Kit (R&D SYSTEM, Cat #WL1000), the human erythrocytes in the isolated PBMC cells were lyzed, and the T cells were enriched following the instruction of operations of Human Cell Enrichment Columns (R&D SYSTEM, Cat #HTCC-10). One portion of $1.0 \times 10^6$ enriched T cells was re-suspended in 250 µL PBS buffer, and washed twice with PBS buffer. An anti-CD3 single-chain antibody was added to give a final concentration of 30 µg/mL and incubated at room temperature for 1 hour. After incubation, the cells were washed twice with PBS, and then 250 μL of Anti-His-tag-ALEXA FLUOR 488 antibody that was 1:2000 diluted was added and incubated at room temperature for 1 hour. After incubation, the cells were washed thrice with PBS buffer, re-suspended in 300 μL PBS buffer, detected by flow cytometer and found that the CD3+ rate in the enriched T cells was 93.5%.

2. Detection of Cytotoxic Effect of Bispecific Antibodies on 786-0 and A375 Cells Mediated by T Cells 786-0 cells in the logarithmic growth phase were trypsinised. The cells were harvested by centrifugation at 1000 rpm for 5 min, and washed twice with PBS buffer. $1.0 \times 10^6$ cells were re-suspended in 1 mL PBS buffer, and a Calcein-AM solution was added to give a final concentration of 2.5 μM. The cells were incubated at 37° C. for 30 min. After incubation, the cells were washed thrice with PBS, and diluted to $5.0 \times 10^5$ in RPMI-1640 medium. 50 μL per well was added to a U-shaped 96-well plate, and then 50 μL of a test sample was added. For the blank control group, 50 μL of RPMI-1640 medium was added; for the positive control group, 50 μL of 3% TRITON-100 was added; and for the test groups, 50 μL of anti-CD26-scFv ($10^1$ pg/mL, $10^3$ pg/mL, $10^4$ pg/mL, $10^5$ pg/mL), 50 μL of BsAb2 ($10^{-1}$ pg/mL, $10^0$ pg/mL, $10^1$ pg/mL, $10^2$ pg/mL, $10^3$ pg/mL, $10^4$ pg/mL, $10^5$ pg/mL, $10^6$ pg/mL), and 50 μL of BsAb4 ($10^{-1}$ pg/mL, $10^0$ pg/mL, $10^1$ pg/mL, $10^2$ pg/mL, $10^3$ pg/mL, $10^4$ pg/mL, $10^5$ pg/mL, $10^6$ pg/mL) were added respectively. The cells were incubated at 37° C. for 30 min. After incubation, T cells were added at a ratio of 786-0: T cell=1:5, and continuously incubated at 37° C. for 7 hours. After incubation, a suitable amount of cell culture supernatant was removed and detected on a microplate reader at an excitation wavelength of 485 nm and an emission wavelength of 515 nm.

A375 cells in the logarithmic growth phase were trypsinized, and washed twice with PBS $1.0 \times 10^6$ cells were re-suspended in 1 mL PBS, and a Calcein-AM solution was added to give a final concentration of 2.5 μM. The cells were incubated at 37° C. for 30 min, then washed thrice with PBS buffer, and diluted to $5.0 \times 10^5$ in DMEM medium. 50 μL per well was added to a U-shaped 96-well plate, and then 50 μL of a test sample was added. For the blank control group, 50 μL of RPMI-1640 medium was added; for the positive control group, 50 μL of 3% TRITON-100 was added; and for the test groups, 50 μL of anti-CD26-scFv ($10^4$ pg/mL), 50 μL of BsAb2 ($10^4$ pg/mL), and 50 μL of BsAb4 ($10^4$ pg/mL) were added respectively. The cells were incubated at 37° C. for 30 min. After incubation, T cells were added at a ratio of A375:T cell=1:5, and continuously incubated at 37° C. for 7 hours. After incubation, a suitable amount of cell culture supernatant was removed and detected on a microplate reader at an excitation wavelength of 485 nm and an emission wavelength of 515 nm.

Test result: The result is shown in Table 5 and FIG. 16. The parent single-chain antibody anti-CD26-scFv, and the BsAb2 and BsAb4 have a lysis rate for the negative control A375 of 1.2%, 2.0%, and 1.5% at $10^4$ pg/mL respectively. The cytotoxic effect of BsAb2 and BsAb4 on 786-0 cells at various concentrations is shown in Table 4.

Conclusions: Compared with the negative control, anti-CD26-scFv, BsAb2, and BsAb4 have an cytotoxic effect on 786-0 cells; however, the parent single-chain antibody anti-CD26-scFv has no obvious concentration-dependent cytotoxic effect on 786-0 cells. Compared with the parent single-chain antibody anti-CD26-scFv, the killing effect of BsAb2, and BsAb4 on 786-0 cells is obviously concentration dependent (FIG. 16). By using GraphPad Prism 5.0 software, BsAb2 is calculated to have an $IC_{50}$ of 1.388 ng/mL, and BsAb4 is calculated to have an $IC_{50}$ of 3.096 ng/mL.

EXAMPLE 13

Detection of Cytotoxic Effect of PBMC on Other Tumor Cells Highly Expressing CD26 Mediated by Bispecific Antibodies Test method: NCI-H2452, PC-3, Caki-1, and COLO205 cells in the logarithmic growth phase were trypsinized. The cells were harvested by centrifugation at 1000 rpm for 5 min, and washed twice with PBS. $1.0 \times 10^6$ cells were re-suspended in 1 mL PBS, and a Calcein-AM solution was added to give a final concentration of 2.5 μM. The cells were incubated at 37° C. for 30 min. After incubation, the cells were washed thrice with PBS, and diluted to $4.5 \times 10$) in RPMI-1640 medium. 50 μL per well was added to a U-shaped 96-well plate, and then 50 μL of a test sample was added. For the blank control group, 50 μL of RPMI-1640 medium was added; for the positive control group, 50 μL of 3% TRITON-100 was added; and for the test groups, 50 μL of 10 ng/mL BsAb1, BsAb2, BsAb3, and BsAb4 were added respectively. The cells were incubated at 37° C. for 30 min. After incubation, PBMC cells were added at a ratio of NCI-H2452/PC-3/Caki-1/COLO205: PBMC=1:15, and continuously incubated at 37° C. for 5 hours. After incubation, a suitable amount of cell culture supernatant was removed and detected on a microplate reader at an excitation wavelength of 485 nm and an emission wavelength of 515 nm.

Test result: The result is shown in Table 6.

TABLE 6

Cytotoxic effect of PBMC on other tumor cells highly expressing CD26 mediated by bispecific antibodies

| Lysis rate (%) | NCI-H2452 | PC-3 | Caki-1 | COLO205 |
| --- | --- | --- | --- | --- |
| BsAb1 | 0.2 | 45.4 | 0.3 | 1.7 |
| BsAb2 | 32.3 | 39.6 | 26.5 | 17.0 |
| BsAb3 | 0.7 | 1.7 | 0.8 | 5.3 |
| BsAb4 | 0.5 | 53.1 | 0.9 | 5.4 |

The test result suggests that all of the bispecific antibodies BsAb1, BsAb2, BsAb3, BsAb4 at 10 ng/mL can mediate PBMC to produce a cytotoxic effect cells on tumor cell lines highly expressing CD26.

TABLE 5

Cytotoxic effect of various concentrations of bispecific antibodies on 786-0 cells

| Lysis rate (%) | $10^6$ pg/mL | $10^5$ pg/mL | $10^4$ pg/mL | $10^3$ pg/mL | $10^2$ pg/mL | $10^1$ pg/mL | $10^0$ pg/mL | $10^{-1}$ pg/mL |
| --- | --- | --- | --- | --- | --- | --- | --- | --- |
| Anti-CD26-scFv | — | 7.5 | 10.9 | 9.6 | 10.8 | — | — | — |
| BsAb2 | 75.1 | 76.3 | 69.6 | 59.2 | 21.8 | 12.9 | 13.4 | 14.3 |
| BsAb4 | 76.4 | 75.4 | 64.8 | 38.8 | 24.3 | 17.7 | 9.3 | 9.5 |

Conclusions: The anti-human CD3×anti-human CD26 bispecific antibodies provided in the present invention can effectively mediate PBMC to produce a cytotoxic effect cells on tumor cells with high expression of CD26 on their surfaces. Moreover, the activity of the bispecific antibodies is affected to some degree with varying structures. Among the anti-human CD3×anti-human CD26 bispecific antibodies having different structures, BsAb2 and BsAb4 have a higher biological activity.

What is claimed is:

1. A bispecific antibody molecule, comprising a variable domain fragment of an antibody that specifically binds to human CD26, and a variable domain fragment of an antibody that specifically binds to human CD3,
   wherein the variable domain fragment that specifically binds to human CD26 comprises a first heavy chain variable domain comprising SEQ ID NO: 1 that specifically binds to human CD26 and a first light chain variable domain comprising SEQ ID NO: 2 that specifically binds to human CD26; and
   wherein the variable domain fragment that specifically binds to human CD3 comprises a second heavy chain variable domain comprising SEQ ID NO: 4 that specifically binds to human CD3 and a second light chain variable domain comprising SEQ ID NO: 5 that specifically binds to human CD3.

2. The bispecific antibody molecule according to claim 1, wherein the first heavy chain variable domain is adjacent to the second heavy chain variable domain; or the first light chain variable domain is adjacent to the second light chain variable domain.

3. The bispecific antibody molecule according to claim 2, having a polypeptide chain comprising from N-terminus to C-terminus:
   a) the first light chain variable domain, the first heavy chain variable domain, the second heavy chain variable domain, and the second light chain variable domain; or
   b) the first heavy chain variable domain, the first light chain variable domain, the second light chain variable domain, and the second heavy chain variable domain.

4. The bispecific antibody molecule according to claim 1, having an amino acid sequence comprising SEQ ID NO: 7, SEQ ID NO: 8, SEQ ID NO: 9 or SEQ ID NO: 10.

5. A method of treating a tumor with high expression of CD26 comprising administering the bispecific antibody molecule of claim 1 to a subject in need thereof.

6. The method according to claim 5, wherein the tumor is renal cancer, prostatic cancer, colon cancer, or mesothelioma.

7. The bispecific antibody molecule according to claim 1, wherein the first heavy chain variable domain is adjacent to the second heavy chain variable domain.

8. The bispecific antibody molecule according to claim 2, having a polypeptide chain comprising from N-terminus to C-terminus, the first light chain variable domain, the first heavy chain variable domain, the second heavy chain variable domain, and the second light chain variable domain.

* * * * *

SEQUENCE LISTING

<160> NUMBER OF SEQ ID NOS: 45

<210> SEQ ID NO 1
<211> LENGTH: 117
<212> TYPE: PRT
<213> ORGANISM: Homo sapiens

<400> SEQUENCE: 1

```
Glu Val Gln Leu Val Glu Ser Gly Ala Gly Val Lys Gln Pro Gly Gly
1               5                   10                  15

Thr Leu Arg Leu Thr Cys Thr Ala Ser Gly Phe Ser Leu Thr Thr Tyr
            20                  25                  30

Gly Val His Trp Val Arg Gln Ala Pro Gly Lys Gly Leu Glu Trp Val
        35                  40                  45

Gly Val Ile Trp Gly Asp Gly Arg Thr Asp Tyr Asp Ala Ala Phe Met
    50                  55                  60

Ser Arg Val Thr Ile Ser Lys Asp Thr Ser Lys Ser Thr Val Tyr Leu
65                  70                  75                  80

Gln Met Asn Ser Leu Arg Ala Glu Asp Thr Ala Val Tyr Tyr Cys Met
                85                  90                  95

Arg Asn Arg His Asp Trp Phe Asp Tyr Trp Gly Gln Gly Thr Thr Val
            100                 105                 110

Thr Val Ser Ser Gly
            115
```

<210> SEQ ID NO 2
<211> LENGTH: 107
<212> TYPE: PRT
<213> ORGANISM: Homo sapiens

<400> SEQUENCE: 2

```
Asp Ile Leu Leu Thr Gln Ser Pro Ser Ser Leu Ser Ala Thr Pro Gly
1               5                   10                  15

Glu Arg Ala Thr Ile Thr Cys Arg Ala Ser Gln Gly Ile Arg Asn Asn
            20                  25                  30

Leu Asn Trp Tyr Gln Gln Lys Pro Gly Gln Ala Pro Arg Leu Leu Ile
        35                  40                  45

Tyr Tyr Ser Ser Asn Leu Gln Ser Gly Val Pro Ser Arg Phe Ser Gly
    50                  55                  60

Ser Gly Ser Gly Thr Asp Phe Thr Leu Thr Ile Ser Arg Leu Gln Pro
65                  70                  75                  80

Glu Asp Val Ala Ala Tyr Tyr Cys Gln Gln Ser Ile Lys Leu Pro Phe
                85                  90                  95

Thr Phe Gly Ser Gly Thr Lys Val Glu Ile Lys
            100                 105
```

<210> SEQ ID NO 3
<211> LENGTH: 14
<212> TYPE: PRT
<213> ORGANISM: Artificial Sequence
<220> FEATURE:
<223> OTHER INFORMATION: Synthetic: polypeptide

<400> SEQUENCE: 3

Gly Gly Gly Ser Gly Gly Gly Ser Gly Gly Gly Ser
1               5               10

<210> SEQ ID NO 4
<211> LENGTH: 120
<212> TYPE: PRT
<213> ORGANISM: Homo sapiens

<400> SEQUENCE: 4

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly
        115                 120

<210> SEQ ID NO 5
<211> LENGTH: 108
<212> TYPE: PRT
<213> ORGANISM: Homo sapiens

<400> SEQUENCE: 5

Ala Asp Asp Ile Val Leu Thr Gln Ser Pro Ala Thr Leu Ser Leu Ser
1               5                   10                  15

Pro Gly Glu Arg Ala Thr Leu Ser Cys Arg Ala Ser Gln Ser Val Ser
            20                  25                  30

Tyr Met Asn Trp Tyr Gln Gln Lys Pro Gly Lys Ala Pro Lys Arg Trp
        35                  40                  45

Ile Tyr Asp Thr Ser Lys Val Ala Ser Gly Val Pro Ala Arg Phe Ser
    50                  55                  60

Gly Ser Gly Ser Gly Thr Asp Tyr Ser Leu Thr Ile Asn Ser Leu Glu
65                  70                  75                  80

Ala Glu Asp Ala Ala Thr Tyr Tyr Cys Gln Gln Trp Ser Ser Asn Pro
                85                  90                  95

Leu Thr Phe Gly Gly Gly Thr Lys Val Glu Ile Lys
            100                 105

<210> SEQ ID NO 6
<211> LENGTH: 15
<212> TYPE: PRT
<213> ORGANISM: Artificial Sequence
<220> FEATURE:
<223> OTHER INFORMATION: Synthetic: polypeptide

<400> SEQUENCE: 6

Glu Gly Thr Ser Thr Gly Ser Gly Gly Ser Gly Gly Ser Gly Gly
1               5                   10                  15

<210> SEQ ID NO 7
<211> LENGTH: 487
<212> TYPE: PRT
<213> ORGANISM: Homo sapiens

<400> SEQUENCE: 7

```
Glu Val Gln Leu Val Glu Ser Gly Ala Gly Val Lys Gln Pro Gly Gly
1               5                   10                  15

Thr Leu Arg Leu Thr Cys Thr Ala Ser Gly Phe Ser Leu Thr Thr Tyr
            20                  25                  30

Gly Val His Trp Val Arg Gln Ala Pro Gly Lys Gly Leu Glu Trp Val
        35                  40                  45

Gly Val Ile Trp Gly Asp Gly Arg Thr Asp Tyr Asp Ala Ala Phe Met
    50                  55                  60

Ser Arg Val Thr Ile Ser Lys Asp Thr Ser Lys Ser Thr Val Tyr Leu
65                  70                  75                  80

Gln Met Asn Ser Leu Arg Ala Glu Asp Thr Ala Val Tyr Tyr Cys Met
                85                  90                  95

Arg Asn Arg His Asp Trp Phe Asp Tyr Trp Gly Gln Gly Thr Thr Val
            100                 105                 110

Thr Val Ser Ser Gly Gly Gly Gly Ser Gly Gly Gly Gly Ser Gly Gly
        115                 120                 125

Gly Gly Ser Asp Ile Leu Leu Thr Gln Ser Pro Ser Ser Leu Ser Ala
    130                 135                 140

Thr Pro Gly Glu Arg Ala Thr Ile Thr Cys Arg Ala Ser Gln Gly Ile
145                 150                 155                 160

Arg Asn Asn Leu Asn Trp Tyr Gln Gln Lys Pro Gly Gln Ala Pro Arg
                165                 170                 175

Leu Leu Ile Tyr Tyr Ser Ser Asn Leu Gln Ser Gly Val Pro Ser Arg
            180                 185                 190

Phe Ser Gly Ser Gly Ser Gly Thr Asp Phe Thr Leu Thr Ile Ser Arg
        195                 200                 205

Leu Gln Pro Glu Asp Val Ala Ala Tyr Tyr Cys Gln Gln Ser Ile Lys
    210                 215                 220

Leu Pro Phe Thr Phe Gly Ser Gly Thr Lys Val Glu Ile Lys Ser Gly
225                 230                 235                 240

Gly Gly Gly Ser Asp Val Gln Leu Val Gln Ser Gly Ala Glu Val Lys
                245                 250                 255

Lys Pro Gly Ala Ser Val Lys Val Ser Cys Lys Ala Ser Gly Tyr Thr
            260                 265                 270

Phe Thr Arg Tyr Thr Met His Trp Val Arg Gln Ala Pro Gly Gln Gly
        275                 280                 285

Leu Glu Trp Ile Gly Tyr Ile Asn Pro Ser Arg Gly Tyr Thr Asn Tyr
    290                 295                 300

Ala Asp Ser Val Lys Gly Arg Phe Thr Ile Thr Thr Asp Lys Ser Thr
305                 310                 315                 320

Ser Thr Ala Tyr Met Glu Leu Ser Ser Leu Arg Ser Glu Asp Thr Ala
                325                 330                 335

Thr Tyr Tyr Cys Ala Arg Tyr Tyr Asp Asp His Tyr Cys Leu Asp Tyr
            340                 345                 350

Trp Gly Gln Gly Thr Thr Val Thr Val Ser Ser Gly Glu Gly Thr Ser
        355                 360                 365

Thr Gly Ser Gly Gly Ser Gly Ser Gly Gly Ala Asp Asp Ile Val
    370                 375                 380
```

-continued

```
Leu Thr Gln Ser Pro Ala Thr Leu Ser Leu Ser Pro Gly Glu Arg Ala
385                 390                 395                 400

Thr Leu Ser Cys Arg Ala Ser Gln Ser Val Ser Tyr Met Asn Trp Tyr
            405                 410                 415

Gln Gln Lys Pro Gly Lys Ala Pro Lys Arg Trp Ile Tyr Asp Thr Ser
        420                 425                 430

Lys Val Ala Ser Gly Val Pro Ala Arg Phe Ser Gly Ser Gly Ser Gly
    435                 440                 445

Thr Asp Tyr Ser Leu Thr Ile Asn Ser Leu Glu Ala Glu Asp Ala Ala
    450                 455                 460

Thr Tyr Tyr Cys Gln Gln Trp Ser Ser Asn Pro Leu Thr Phe Gly Gly
465                 470                 475                 480

Gly Thr Lys Val Glu Ile Lys
                485

<210> SEQ ID NO 8
<211> LENGTH: 486
<212> TYPE: PRT
<213> ORGANISM: Homo sapiens

<400> SEQUENCE: 8

Asp Ile Leu Leu Thr Gln Ser Pro Ser Ser Leu Ser Ala Thr Pro Gly
1               5                   10                  15

Glu Arg Ala Thr Ile Thr Cys Arg Ala Ser Gln Gly Ile Arg Asn Asn
            20                  25                  30

Leu Asn Trp Tyr Gln Gln Lys Pro Gly Gln Ala Pro Arg Leu Leu Ile
        35                  40                  45

Tyr Tyr Ser Ser Asn Leu Gln Ser Gly Val Pro Ser Arg Phe Ser Gly
    50                  55                  60

Ser Gly Ser Gly Thr Asp Phe Thr Leu Thr Ile Ser Arg Leu Gln Pro
65                  70                  75                  80

Glu Asp Val Ala Ala Tyr Tyr Cys Gln Gln Ser Ile Lys Leu Pro Phe
                85                  90                  95

Thr Phe Gly Ser Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Ala Gly Val Lys Gln Pro Gly Gly Thr Leu Arg Leu Thr Cys
130                 135                 140

Thr Ala Ser Gly Phe Ser Leu Thr Thr Tyr Gly Val His Trp Val Arg
145                 150                 155                 160

Gln Ala Pro Gly Lys Gly Leu Glu Trp Val Gly Val Ile Trp Gly Asp
            165                 170                 175

Gly Arg Thr Asp Tyr Asp Ala Ala Phe Met Ser Arg Val Thr Ile Ser
        180                 185                 190

Lys Asp Thr Ser Lys Ser Thr Val Tyr Leu Gln Met Asn Ser Leu Arg
    195                 200                 205

Ala Glu Asp Thr Ala Val Tyr Tyr Cys Met Arg Asn Arg His Asp Trp
210                 215                 220

Phe Asp Tyr Trp Gly Gln Gly Thr Thr Val Thr Val Ser Ser Gly Gly
225                 230                 235                 240

Gly Gly Ser Asp Val Gln Leu Val Gln Ser Gly Ala Glu Val Lys Lys
            245                 250                 255

Pro Gly Ala Ser Val Lys Val Ser Cys Lys Ala Ser Gly Tyr Thr Phe
        260                 265                 270
```

```
Thr Arg Tyr Thr Met His Trp Val Arg Gln Ala Pro Gly Gln Gly Leu
            275                 280                 285

Glu Trp Ile Gly Tyr Ile Asn Pro Ser Arg Gly Tyr Thr Asn Tyr Ala
    290                 295                 300

Asp Ser Val Lys Gly Arg Phe Thr Ile Thr Thr Asp Lys Ser Thr Ser
305                 310                 315                 320

Thr Ala Tyr Met Glu Leu Ser Ser Leu Arg Ser Glu Asp Thr Ala Thr
                325                 330                 335

Tyr Tyr Cys Ala Arg Tyr Tyr Asp Asp His Tyr Cys Leu Asp Tyr Trp
            340                 345                 350

Gly Gln Gly Thr Thr Val Thr Val Ser Ser Gly Glu Gly Thr Ser Thr
            355                 360                 365

Gly Ser Gly Gly Ser Gly Gly Ser Gly Gly Ala Asp Asp Ile Val Leu
        370                 375                 380

Thr Gln Ser Pro Ala Thr Leu Ser Leu Ser Pro Gly Glu Arg Ala Thr
385                 390                 395                 400

Leu Ser Cys Arg Ala Ser Gln Ser Val Ser Tyr Met Asn Trp Tyr Gln
                405                 410                 415

Gln Lys Pro Gly Lys Ala Pro Lys Arg Trp Ile Tyr Asp Thr Ser Lys
            420                 425                 430

Val Ala Ser Gly Val Pro Ala Arg Phe Ser Gly Ser Gly Ser Gly Thr
            435                 440                 445

Asp Tyr Ser Leu Thr Ile Asn Ser Leu Glu Ala Glu Asp Ala Ala Thr
        450                 455                 460

Tyr Tyr Cys Gln Gln Trp Ser Ser Asn Pro Leu Thr Phe Gly Gly Gly
465                 470                 475                 480

Thr Lys Val Glu Ile Lys
                485

<210> SEQ ID NO 9
<211> LENGTH: 487
<212> TYPE: PRT
<213> ORGANISM: Homo sapiens

<400> SEQUENCE: 9

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
```

145                 150                 155                 160
Arg Ala Ser Gln Ser Val Ser Tyr Met Asn Trp Tyr Gln Gln Lys Pro
                    165                 170                 175

Gly Lys Ala Pro Lys Arg Trp Ile Tyr Asp Thr Ser Lys Val Ala Ser
                180                 185                 190

Gly Val Pro Ala Arg Phe Ser Gly Ser Gly Ser Gly Thr Asp Tyr Ser
            195                 200                 205

Leu Thr Ile Asn Ser Leu Glu Ala Glu Asp Ala Ala Thr Tyr Tyr Cys
        210                 215                 220

Gln Gln Trp Ser Ser Asn Pro Leu Thr Phe Gly Gly Gly Thr Lys Val
225                 230                 235                 240

Glu Ile Lys Ser Gly Gly Gly Gly Ser Glu Val Gln Leu Val Glu Ser
                245                 250                 255

Gly Ala Gly Val Lys Gln Pro Gly Gly Thr Leu Arg Leu Thr Cys Thr
                    260                 265                 270

Ala Ser Gly Phe Ser Leu Thr Thr Tyr Gly Val His Trp Val Arg Gln
            275                 280                 285

Ala Pro Gly Lys Gly Leu Glu Trp Val Gly Val Ile Trp Gly Asp Gly
        290                 295                 300

Arg Thr Asp Tyr Asp Ala Ala Phe Met Ser Arg Val Thr Ile Ser Lys
305                 310                 315                 320

Asp Thr Ser Lys Ser Thr Val Tyr Leu Gln Met Asn Ser Leu Arg Ala
                325                 330                 335

Glu Asp Thr Ala Val Tyr Tyr Cys Met Arg Asn Arg His Asp Trp Phe
                    340                 345                 350

Asp Tyr Trp Gly Gln Gly Thr Thr Val Thr Val Ser Ser Gly Gly Gly
            355                 360                 365

Gly Ser Gly Gly Gly Gly Ser Gly Gly Gly Gly Ser Asp Ile Leu Leu
        370                 375                 380

Thr Gln Ser Pro Ser Ser Leu Ser Ala Thr Pro Gly Glu Arg Ala Thr
385                 390                 395                 400

Ile Thr Cys Arg Ala Ser Gln Gly Ile Arg Asn Asn Leu Asn Trp Tyr
                405                 410                 415

Gln Gln Lys Pro Gly Gln Ala Pro Arg Leu Leu Ile Tyr Tyr Ser Ser
                    420                 425                 430

Asn Leu Gln Ser Gly Val Pro Ser Arg Phe Ser Gly Ser Gly Ser Gly
            435                 440                 445

Thr Asp Phe Thr Leu Thr Ile Ser Arg Leu Gln Pro Glu Asp Val Ala
        450                 455                 460

Ala Tyr Tyr Cys Gln Gln Ser Ile Lys Leu Pro Phe Thr Phe Gly Ser
465                 470                 475                 480

Gly Thr Lys Val Glu Ile Lys
                485

<210> SEQ ID NO 10
<211> LENGTH: 487
<212> TYPE: PRT
<213> ORGANISM: Homo sapiens

<400> SEQUENCE: 10

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

```
Thr Met His Trp Val Arg Gln Ala Pro Gly Gln Gly Leu Glu Trp Ile
         35                  40                  45
Gly Tyr Ile Asn Pro Ser Arg Gly Tyr Thr Asn Tyr Ala Asp Ser Val
 50                  55                  60
Lys Gly Arg Phe Thr Ile Thr Thr Asp Lys Ser Thr Ser Thr Ala Tyr
 65                  70                  75                  80
Met Glu Leu Ser Ser Leu Arg Ser Glu Asp Thr Ala Thr Tyr Tyr Cys
                 85                  90                  95
Ala Arg Tyr Tyr Asp Asp His Tyr Cys Leu Asp Tyr Trp Gly Gln Gly
            100                 105                 110
Thr Thr Val Thr Val Ser Ser Gly Glu Gly Thr Ser Thr Gly Ser Gly
            115                 120                 125
Gly Ser Gly Gly Ser Gly Gly Ala Asp Asp Ile Val Leu Thr Gln Ser
130                 135                 140
Pro Ala Thr Leu Ser Leu Ser Pro Gly Glu Arg Ala Thr Leu Ser Cys
145                 150                 155                 160
Arg Ala Ser Gln Ser Val Ser Tyr Met Asn Trp Tyr Gln Gln Lys Pro
                165                 170                 175
Gly Lys Ala Pro Lys Arg Trp Ile Tyr Asp Thr Ser Lys Val Ala Ser
            180                 185                 190
Gly Val Pro Ala Arg Phe Ser Gly Ser Gly Ser Gly Thr Asp Tyr Ser
            195                 200                 205
Leu Thr Ile Asn Ser Leu Glu Ala Glu Asp Ala Ala Thr Tyr Tyr Cys
        210                 215                 220
Gln Gln Trp Ser Ser Asn Pro Leu Thr Phe Gly Gly Gly Thr Lys Val
225                 230                 235                 240
Glu Ile Lys Ser Gly Gly Gly Ser Asp Ile Leu Leu Thr Gln Ser
                245                 250                 255
Pro Ser Ser Leu Ser Ala Thr Pro Gly Glu Arg Ala Thr Ile Thr Cys
            260                 265                 270
Arg Ala Ser Gln Gly Ile Arg Asn Asn Leu Asn Trp Tyr Gln Gln Lys
            275                 280                 285
Pro Gly Gln Ala Pro Arg Leu Leu Ile Tyr Tyr Ser Ser Asn Leu Gln
        290                 295                 300
Ser Gly Val Pro Ser Arg Phe Ser Gly Ser Gly Ser Gly Thr Asp Phe
305                 310                 315                 320
Thr Leu Thr Ile Ser Arg Leu Gln Pro Glu Asp Val Ala Ala Tyr Tyr
                325                 330                 335
Cys Gln Gln Ser Ile Lys Leu Pro Phe Thr Phe Gly Ser Gly Thr Lys
            340                 345                 350
Val Glu Ile Lys Gly Gly Gly Gly Ser Gly Gly Gly Gly Ser Gly Gly
            355                 360                 365
Gly Gly Ser Glu Val Gln Leu Val Glu Ser Gly Ala Gly Val Lys Gln
        370                 375                 380
Pro Gly Gly Thr Leu Arg Leu Thr Cys Thr Ala Ser Gly Phe Ser Leu
385                 390                 395                 400
Thr Thr Tyr Gly Val His Trp Val Arg Gln Ala Pro Gly Lys Gly Leu
                405                 410                 415
Glu Trp Val Gly Val Ile Trp Gly Asp Gly Arg Thr Asp Tyr Asp Ala
            420                 425                 430
Ala Phe Met Ser Arg Val Thr Ile Ser Lys Asp Thr Ser Lys Ser Thr
            435                 440                 445
Val Tyr Leu Gln Met Asn Ser Leu Arg Ala Glu Asp Thr Ala Val Tyr
```

```
                    450                 455                 460
Tyr Cys Met Arg Asn Arg His Asp Trp Phe Asp Tyr Trp Gly Gln Gly
465                 470                 475                 480

Thr Thr Val Thr Val Ser Ser
                485

<210> SEQ ID NO 11
<211> LENGTH: 18
<212> TYPE: PRT
<213> ORGANISM: Artificial Sequence
<220> FEATURE:
<223> OTHER INFORMATION: Synthetic: sandfly yellow-related protein

<400> SEQUENCE: 11

Met Arg Phe Phe Phe Val Phe Leu Ala Ile Val Leu Phe Gln Gly Ile
1               5                   10                  15

His Gly

<210> SEQ ID NO 12
<211> LENGTH: 16
<212> TYPE: PRT
<213> ORGANISM: Artificial Sequence
<220> FEATURE:
<223> OTHER INFORMATION: Synthetic: Silkworm fibroin-related protein

<400> SEQUENCE: 12

Met Lys Pro Ile Phe Leu Val Leu Leu Val Val Thr Ser Ala Tyr Ala
1               5                   10                  15

<210> SEQ ID NO 13
<211> LENGTH: 18
<212> TYPE: PRT
<213> ORGANISM: Cypridina noctiluca

<400> SEQUENCE: 13

Met Lys Thr Leu Ile Leu Ala Val Ala Leu Val Tyr Cys Ala Thr Val
1               5                   10                  15

His Cys

<210> SEQ ID NO 14
<211> LENGTH: 17
<212> TYPE: PRT
<213> ORGANISM: Artificial Sequence
<220> FEATURE:
<223> OTHER INFORMATION: Synthetic: pinemoth-related protein

<400> SEQUENCE: 14

Met Met Arg Pro Ile Val Leu Val Leu Leu Phe Ala Thr Ser Ala Leu
1               5                   10                  15

Ala

<210> SEQ ID NO 15
<211> LENGTH: 6
<212> TYPE: PRT
<213> ORGANISM: Artificial Sequence
<220> FEATURE:
<223> OTHER INFORMATION: Synthetic: Tag

<400> SEQUENCE: 15

His His His His His His
1               5

<210> SEQ ID NO 16
```

```
<211> LENGTH: 1539
<212> TYPE: DNA
<213> ORGANISM: Homo sapiens

<400> SEQUENCE: 16
atgcgttttt tctttgtttt cttagctatt gtcttgtttc aaggtatcca tggcgaagtt      60
caattagtcg agtctggtgc tggcgtaaaa cagcctggag ggactttgcg tcttacctgt     120
acagcctccg ttttttcact cacgactttat ggcgtgcatt gggttcgcca agcacccgga    180
aaggggctag aatgggtcgg tgtaatttgg ggcgatggac gaaccgacta cgatgcggct     240
ttcatgtcgc gggtgacaat cagtaaagac acgagcaagt ctactgttta tctgcagatg     300
aattccttaa gagccgagga taccgcagtc tactattgca tgaggaaccg tcacgactgg     360
tttgattact gggggcaagg tacaacggta actgtgtcat cggcggagg gggtagtggc      420 ggaggggta gcggcggagg gggttctgac atattgctta cccagtcccc atcatcgctc     480
agtgcgacac cgggcgaacg cgctacgatt acttgtcgag ccagccaagg aatccggaat    540
aacctaaatt ggtatcagca aaaacctggg caggcaccca gactgttaat atactattct     600
tccaacttgc aatcaggtgt tccatcgagg ttcagtggca gcggatctgg gaccgatttt    660
acacttacga tttcccgtct ccagccgag gacgtcgcgg cttactattg ccaacagtca     720
atcaagctac ctttcacttt tggttcgggc accaaagtag aaataaagag tggaggggt     780 ggcagcgatg tgcaactggt tcagtctgga gccgaggtca aaaagcccgg gcatccgta     840 aaagtgtcat gtaaggcgtc gggttacaca ttcacgcgct atactatgca ttgggttcga    900
caagctccag gccagggatt agaatggatt gggtacatca atccgagtcg ggttatacc    960 aactacgccg acagcgtcaa aggcagattt acaataacga ctgataagtc tacctccaca    1020
gcatatatgg agttgtcatc gcttaggagt gaagacacgg cgacttacta ttgcgctcgt    1080
tactatgatg accactactg tctcgattat tggggacaag gaccacagt aacggtgagc     1140 tctggtgagg gcacttccac cggatcaggg ggttcgggcg aagtgggggg tgccgacgat    1200
attgttctaa cacagagccc tgcaacgctg tctttatccc ccggcgaacg cgcgactttg    1260
tcatgccgag cttcgcaaag tgtcagctac atgaattggt atcagcaaaa accaggaaag    1320
gccccgaaac ggtggatcta cgacacctct aaggtagcat ccggggtgcc tgcgagattc    1380
tcaggttcgg gcagtggaac agattatagc cttacgataa actctctcga ggctgaagac    1440
gccgcaactt actattgtca gcaatggtcc tcaaatcccc taacctttgg gggtggcaca    1500
aaagttgaga ttaagcatca ccatcaccat cactgataa                           1539

<210> SEQ ID NO 17
<211> LENGTH: 1530
<212> TYPE: DNA
<213> ORGANISM: Homo sapiens

<400> SEQUENCE: 17
atgaaaccta ttttttttagt tttgcttgtc gtaacttctg cttatgccga tatttttattg    60 actcaatctc cttcctcact ttcggctacc cccggtgaac gtgccacaat cacgtgtcgc    120
gcaagtcagg gcatacgaaa taacctcaat tggtatcaac agaaaccagg acaagcgccg    180
cggctactga tttactatag ctctaactta cagtccgggg ttccttcaag atttttcgggt    240 agtggcagcg gaactgactt caccttgaca atctctaggc ttcaaccgga ggatgtcgct    300
gcctactatt gccagcaatc cataaagctc ccatttacgt tcgggtcagg tactaaagta    360
gaaattaagg gcggaggggg ttcgggcgga gggggtagtg gcggaggggg tagcgaggtg    420
```

```
cagctagttg aatctggcgc aggagtcaaa caaccggggg gtaccctgcg tttaacatgt        480
acggcgtccg gcttttcatt gactacctac ggagtacatt gggtgcgcca ggctcctggg        540
aagggtcttg agtgggttgg cgtcatctgg ggagacgggc gaacagatta tgacgccgca        600
ttcatgtcgc gggtaacgat aagtaaagat actagcaagt ctaccgtgta cctccaaatg        660
aattccctaa gagcggaaga cacagctgtt tattactgca tgaggaaccg tcacgattgg        720
tttgactatt ggggtcaggg cacgactgtc accgtatcat cggagggggg tggcagtgat        780
gtgcaactgg ttcagagcgg agccgaggtc aaaaagcccg ggcatctgt aaaagtgtcc         840 tgtaaggcgt caggttacac attcacgcgc tatactatgc attgggttcg acaagctcca        900
ggccagggat tagaatggat tgggtacatc aatccgtcgc ggggttatac caactacgcc        960
gacagtgtca aaggcagatt tacaataacg actgataaga gcacctctac agcatatatg       1020
gagttgtcct cacttaggtc ggaagacacg gcgacttact attgcgctcg ttactatgat       1080
gaccactact gtctcgatta ttggggacaa gggaccacag taacggtgag tagcggtgag       1140
ggcacttcta ccggatccgg gggttcaggc ggatcggggg gtgccgacga tattgttcta       1200
acacagagtc ctgcaacgct gagcttatct cccggcgaac gcgcgacttt gtcctgccga       1260
gcttcacaat cggtcagtta catgaattgg tatcagcaaa aaccaggaaa ggccccgaaa       1320
cggtggatct acgacaccag caaggtagca tctggggtgc ctgcgagatt ctccggttca       1380
ggctcgggaa cagattatag tcttacgata aacagcctcg aggctgaaga cgccgcaact       1440
tactattgtc agcaatggtc ttccaatccc ctaacctttg ggggtggcac aaaagttgag       1500
attaagcatc accatcacca tcactgataa                                         1530

<210> SEQ ID NO 18
<211> LENGTH: 1539
<212> TYPE: DNA
<213> ORGANISM: Homo sapiens

<400> SEQUENCE: 18
atgaaaactt taattttggc tgttgccctt gtctattgtg caaccgtaca ttgcgatgtt         60
caattagtcc agtctggtgc tgaagtaaaa aagcctggcg cctccgtgaa agtttcatgt        120
aaggcatcgg gatatacttt tacccgttac acaatgcatt gggtccgcca agcgcccggg        180 cagggttttgg agtggattgg ctatatcaat ccaagtcgag gatacacgaa ctatgctgac       240
agcgtaaaag gcggttcac tataaccaca gataagtcta cgtccactgc ctacatggaa        300
ctttcatcgc tcagaagtga ggacaccgca acatattact gcgcgaggta ttacgatgac       360
cactattgtc tagattactg gggtcaaggc acgactgtga ccgttagctc tggagaaggg       420
acatccacgg gttcagcgg atcgggggt agtggcggag ctgacgatat tgtcctgact        480
cagagcccgg ccaccttatc tttgtcccct ggggagcgtg caacactttc atgccgcgcg       540
tcgcaaagtg taagctatat gaattggtac cagcaaaaac ccgtaaggc tccaaaacga       600 tggatctatg acacgtctaa ggtggcctcc ggcgttccgg cacggttttc aggatcgggg       660
agtggtactg attacagcct caccataaac tctctagaag cggaggacgc tgccacatat       720
tactgtcagc aatggtcctc aaatcctctg acgttcggcg gagggactaa agtcgaaatt       780
aagtcgggtg gcggagggag tgaggtacag ttagtggaaa gcggtgcagg cgttaaacaa       840
cccggaggga ccttgagact acatgcacg gcgtctggtt ttcccctcac tacctatggc      900
gtccattggg taaggcaggc tccaggaaag gggctagagt gggtgggtgt tatctgggc       960
```

```
gatggacgta cagactacga tgccgcattc atgtcacgcg tcacgatatc gaaagacact    1020
agtaagagca ccgtatatct gcaaatgaac tctttacgag cggaagatac agctgtgtac    1080
tattgtatgc ggaatagaca cgactggttt gattactggg ggcagggtac gactgttacc    1140
gtctcctcag gcggaggggg ttcggccgga gggggtagtg gcggaggggg tagcgacatt    1200
ttgcttacac aatctccgtc ctcactctcg gccacgcctg gcgagagggc aactatcacc    1260
tgccgtgcga gtcagggaat acgcaacaat ctaaactggt atcaacagaa acccgggcaa    1320
gctccacgac tgttaattta ctatagctct aatttgcagt ccggtgtacc gtcacggttc    1380
tcgggcagtg gaagcgggac agattttacg cttactatct ctagactcca acctgaagac    1440
gtggccgcat actattgtca gcaatccata aagctaccct tcacctttgg ttcaggcaca    1500
aaagttgaga ttaagcatca ccatcaccat cactgataa                           1539

<210> SEQ ID NO 19
<211> LENGTH: 1536
<212> TYPE: DNA
<213> ORGANISM: Homo sapiens

<400> SEQUENCE: 19
atgatgcgtc ctattgtttt agtcttgctt tttgctactt ctgccctcgc agatgttcaa      60
ttagtccagt ctggtgctga agtaaaaaag cctggcgcct ccgtgaaagt ttcatgtaag     120
gcatcgggat atacttttac ccgttacaca atgcattggg tccgccaagc gcccgggcag     180
ggtttggagt ggattggcta tatcaatcca gtcgaggat acacgaacta tgctgacagc     240
gtaaaagggc ggttcactat aaccacagat aagtctacgt ccactgccta catggaactt     300
tcatcgctca gaagtgagga caccgcaaca tattactgcg cgaggtatta cgatgaccac     360
tattgtctag attactgggg tcaaggcacg actgtgaccg ttagctctgg agaagggaca     420
tccacgggtt caggcggatc ggggggtagt ggcggagctg acgatattgt cctgactcag     480
agcccggcca cctatctttt gtcccctggg gagcgtgcaa cactttcatg ccgcgcgtcg     540
caaagtgtaa gctatatgaa ttggtaccag caaaaacccg gtaaggctcc aaaacgatgg     600
atctatgaca cgtctaaggt ggcctccggc gttccggcac ggttttcagg atcggggagt     660
ggtactgatt acagcctcac cataaactct ctagaagcgg aggacgctgc acatatattac    720 tgtcagcaat ggtcctcaaa tcctctgacg ttcggcggag ggactaaagt cgaaattaag     780
tcgggtggcg gagggagtga tatcttattg acccagagcc cctcttccct ttcagcaaca     840
ccaggtgaga gagcgacgat aacttgcagg gcttcgcaag gcattcgtaa caatctcaac     900
tggtatcagc aaaaaccggg acaggcccct cgcctactga tctactatag tagcaattta     960
caatctgggg taccctcccg attttcaggt tcgggcagtg gaaccgactt cacattgacg    1020
ataagccggc ttcagccaga agatgtggca gcgtactatt gtcaacagtc tattaagctc    1080
ccgtttactt tcgggtccgg taccaaagtt gagatcaagg gcggaggggg ttcaggcgga    1140
gggggttcgg gcggaggggg tagtgaagtc caactagtag agagcggcgc tggagtgaaa    1200
cagcctgggg gtacactgag attaacgtgc actgcctctg gcttttcctt gaccacatac    1260
ggagttcatt gggtcaggca agcacccggg aagggtcttg aatgggtagg cgtgatatgg    1320
ggagacgggc gtacggatta tgacgcggct ttcatgtcac gcgttactat ttcgaaagat    1380
accagtaaga gcacagtcta cctccagatg aactctctac gagccgagga cacggcagta    1440
tattactgta tgcggaatag acacgattgg tttgactatt ggggtcaagg cactaccgtg    1500
acagtttcct cacatcacca tcaccatcac tgataa                               1536
```

<210> SEQ ID NO 20
<211> LENGTH: 1539
<212> TYPE: DNA
<213> ORGANISM: Homo sapiens

<400> SEQUENCE: 20

| | | | | | |
|---|---|---|---|---|---|
| atgagattct | ttttcgtgtt | tctggctatc | gtcctgttcc | agggaattca | cggggaggtg | 60 |
| cagctggtcg | aaagcggtgc | aggagtgaaa | cagccaggag | gaaccctgag | gctgacttgc | 120 |
| accgcttctg | gttttagtct | gaccacatac | ggagtgcatt | gggtccgaca | ggcacctgga | 180 |
| aagggactgg | agtgggtggg | agtcatctgg | ggtgacggac | gcacagacta | cgatgccgct | 240 |
| ttcatgtccc | gagtgactat | tagcaaagac | acatctaaga | gtactgtcta | tctgcagatg | 300 |
| aactctctgc | gcgccgaaga | tactgccgtg | tactattgca | tgaggaatcg | gcacgactgg | 360 |
| tttgattact | ggggacaggg | aactaccgtg | accgtctcca | gcggaggtgg | aggatctgga | 420 |
| ggtggaggaa | gtgggggtgg | cggatcagac | atcctgctga | ctcagtcccc | ttctagtctg | 480 |
| agcgccaccc | caggagagag | agctacaatc | acttgtcgcg | catcccaggg | cattcgaaac | 540 |
| aatctgaact | ggtaccagca | gaagcccgga | caggctcctc | gtctgctgat | ctactattca | 600 |
| tccaatctgc | agagtggcgt | gccttcacgc | ttttcaggtt | ccggcagcgg | aaccgacttc | 660 |
| accctgacaa | tttcccgact | gcagcctgaa | gatgtggcag | cctactattg | ccagcagagt | 720 |
| atcaagctgc | catttacctt | cgggagcggt | acaaaagtgg | agattaagtc | tggggtggc | 780 |
| ggaagtgacg | tgcagctggt | ccagagcgga | gcagaagtca | agaaaccagg | gcctccgtg | 840 |
| aaagtcagct | gtaaggcatc | tggctacact | tttaccaggt | acaccatgca | ctgggtcaga | 900 |
| caggcaccag | gacagggact | ggagtggatc | ggttacatta | cccctctcg | ggggtacacc | 960 |
| aattatgctg | actccgtgaa | aggcagattc | acaatcacaa | ctgataagtc | tacaagtact | 1020 |
| gcatatatgg | agctgagctc | tctgcgttct | gaagacaccg | caacatacta | ttgcgccagg | 1080 |
| tactatgacg | atcattactg | tctggattat | tgggggcagg | gtaccacagt | gaccgtcagt | 1140 |
| tcaggcgagg | gaacttcaac | cggatccgga | ggtagcggag | gatctggagg | tgctgacgat | 1200 |
| attgtgctga | ctcagagccc | agcaaccctg | tcactgtccc | ctggagaacg | tgccacactg | 1260 |
| tcttgcaggg | ctagccagtc | tgtgagttac | atgaactggt | atcagcagaa | gccaggaaaa | 1320 |
| gctcccaaga | ggtggatcta | cgatactagt | aaggtggctt | caggcgtccc | agcacgattt | 1380 |
| tcagggtccg | gtagcggcac | agactattca | ctgactatta | actctctgga | ggccgaagat | 1440 |
| gctgcaacct | actattgtca | gcagtggtcc | agcaatcccc | tgaccttcgg | cggagggaca | 1500 |
| aaagtggaga | tcaagcacca | tcaccatcac | cattgataa | | | 1539 |

<210> SEQ ID NO 21
<211> LENGTH: 1530
<212> TYPE: DNA
<213> ORGANISM: Homo sapiens

<400> SEQUENCE: 21

| | | | | | |
|---|---|---|---|---|---|
| atgaaaccta | tcttcctggt | gctgctggtg | gtcacttccg | cctacgctga | cattctgctg | 60 |
| acccagtccc | cttccagcct | gagcgcaaca | ccaggagaga | gagccactat | cacctgccgc | 120 |
| gctagccagg | gcattcgaaa | caatctgaac | tggtatcagc | agaagcccgg | ccaggctcct | 180 |
| cgtctgctga | tctactattc | tagtaatctg | cagagtggag | tgccatcacg | cttctctggt | 240 |
| agtggctcag | gaacagactt | tacactgact | atttctcgac | tgcagcctga | ggatgtggcc | 300 |

```
gcttactatt gccagcagag tatcaagctg ccattcacct ttgggagcgg tacaaaagtc      360
gaaattaagg gaggaggagg ttccggagga ggaggtagtg gcggagggg ttcagaggtg       420 cagctggtcg aatccggcgc aggagtgaaa cagcccggcg aaccctgag gctgacctgt       480 acagcctctg gattcagtct gaccacatac ggagtgcact gggtccgaca ggcacctgga      540
aagggtctgg agtgggtggg agtcatctgg ggagacggac gcactgacta cgatgcagcc     600
tttatgtccc gagtgaccat tagcaaagac acatccaaga gcactgtcta tctgcagatg      660
aacagcctga gagcagaaga taccgccgtg tactattgca tgaggaatcg gcacgactgg      720
tttgattact gggggcaggg tactaccgtg acagtctcat ccgggggtgg cggatcagat      780
gtgcagctgg tccagtctgg tgctgaggtg aagaaacccg gcgcatccgt gaaagtcagc      840
tgtaaggctt ctggctacac tttcaccagg tacaccatgc attgggtcag acaggcacca      900
ggccagggac tggaatggat cggatacatt aaccccctct cgggggtacac aaattatgct    960 gactccgtga aggcagatt tactatcaca actgataagt ctacaagtac tgcctatatg      1020
gagctgagct ctctgcgttc tgaagacacc gctacatact attgcgcaag gtactatgac    1080
gatcattact gtctggatta ttgggggcag gtaccacag tgaccgtcag ttcaggcgag      1140
ggaacttcaa ccggatccgg aggtagcgga ggatctggag gtgcagacga tattgtgctg    1200
actcagagcc cagctaccct gtcactgtcc cctggagaac gtgcaactct gtcttgcagg    1260
gccagccagt ctgtgagtta catgaattgg taccagcaga agccaggcaa agctcccaag    1320
aggtggatct acgataccag taaggtggcc tcaggcgtcc cagctcgatt ctcagggtcc    1380
ggtagcggca cagactattc tctgactatt aacagtctgg aggccgaaga tgctgcaacc    1440
tactattgtc agcagtggtc cagcaatccc ctgacctttg gcggagggac aaaagtggag    1500
atcaagcacc atcaccatca ccattgataa                                      1530
```

<210> SEQ ID NO 22
<211> LENGTH: 1539
<212> TYPE: DNA
<213> ORGANISM: Homo sapiens

<400> SEQUENCE: 22

```
atgaagactc tgatcctggc cgtggctctg gtctactgcg ccaccgtgca ctgtgacgtg       60
cagctggtcc agagcggagc tgaggtcaag aaacctgggg caagtgtgaa agtctcatgc    120
aaggcttccg gctacacttt caccaggtac accatgcatt gggtcagaca ggcacctggt    180
cagggcctgg aatggatcgg ttacattaac cccgtcgg gctacacaaa ttatgctgac       240
agcgtgaaag gcagatttac tatcaccacc gataagtcta caagtactgc ctatatggag    300
ctgtccagcc tgcgttctga agacaccgct acatactatt gcgcaaggta ctatgacgat    360
cactactgtc tggattattg ggacagggg actaccgtga ccgtctctag tggcgagggc     420
acttctaccg gaagtggagg atcaggaggt tccggaggag cagacgatat tgtgctgacc    480
cagagccctg ctacactgtc actgtcccca ggcgaaagag caaccctgtc ttgtcgcgcc    540
agccagtctg tgagttacat gaactggtat cagcagaagc ccggcaaagc tcctaagagg    600
tggatctacg atacaagcaa ggtggcctct ggagtcccag ctcgattctc aggatccggg    660
agcggtactg actattccct gaccattaac agcctggagg ccgaagatgc cgctacctac    720
tattgccagc agtggtcatc caatcccctg acatttgggg gtggcactaa agtggagatc    780
aagtctggag gggtggcag tgaggtgcag ctggtcgaat ctggcgcagg agtgaaacag    840
cccggaggga cactgaggct gacatgtact gccagcggat tctctctgac aacttacgga    900
```

-continued

```
gtgcactggg tccgacaggc tcctggaaag ggtctggagt gggtgggagt catctgggga    960
gacggacgca ccgactacga tgcagccttt atgtcacgag tgacaatttc caaagacaca   1020
tctaagagta ctgtctatct gcagatgaac tccctgagag cagaagatac agccgtgtac   1080
tattgcatga ggaatcggca tgactggttc gattactggg gcagggtac cacagtgact    1140 gtcagctctg gtggaggagg aagcggtgga ggagggtctg gtggcggagg gagtgatatt   1200
ctgctgactc agtcacccag ttcactgtct gctaccccctg gagagcgagc aaccatcaca   1260
tgtcgtgcct cccagggcat taggaacaat ctgaattggt accagcagaa accaggccag   1320
gccccccgtc tgctgatcta ctattccagc aatctgcaga gtggcgtgcc atcacgcttc   1380
tcaggctccg gaagcgggac cgactttact ctgaccatta ccgactgca gcctgaggat   1440 gtggctgcat actattgcca gcagtctatc aagctgccat tcacctttgg ttccggcaca   1500
aaagtggaaa ttaagcacca tcaccatcac cattgataa                          1539
```

<210> SEQ ID NO 23
<211> LENGTH: 1536
<212> TYPE: DNA
<213> ORGANISM: Homo sapiens

<400> SEQUENCE: 23

```
atgatgagac ccatcgtgct ggtcctgctg ttcgccacca gcgccctggc tgacgtgcag     60
ctggtccagt ctggagctga ggtgaagaaa cctggggcaa gtgtgaaagt ctcatgcaag    120
gcttccggct acactttttac caggtacacc atgcactggg tcagacaggc acctggtcag    180
ggcctggaat ggatcggtta cattaacccc agtcggggct acacaaatta tgctgacagc    240
gtgaaaggca gattcactat caccaccgat aagtctacaa gtactgccta tatggagctg    300
tccagcctgc gtagcgaaga caccgctaca tactattgcg caaggtacta tgacgatcat    360
tactgtctgg attattgggg acaggggact accgtgaccg tctctagtgg cgagggcact    420
tctaccggaa gtgaggatc aggaggttcc ggaggagcag acgatattgt gctgacccag    480 tccccctgcta cactgtcact gtccccaggc gaaagagcaa cactgagctg tcgcgccagc    540
cagtctgtga gttacatgaa ctggtatcag cagaagcccg gcaaagctcc taagaggtgg    600
atctacgaca ctagcaaggt ggcctctgga gtccctgctc gattctcagg atccgggagc    660
ggtactgact attccctgac cattaacagc ctggaggccg aagatgccgc tacctactat    720
tgccagcagt ggtcatccaa tccactgaca tttgggggtg gcactaaagt ggagatcaag    780
tctgaggggg gtggcagtga tattctgctg actcagtcac ccagctctct gtccgctacc    840
cctggagaac gagcaacaat cacttgtcgt gcctctcagg gcattaggaa caatctgaac    900
tggtaccagc agaagccagg ccaggctccc cgtctgctga tctactatag ttcaaatctg    960
cagagtggcg tgccctcacg cttctctggc agtggatcag ggaccgactt taccctgaca   1020 attcccgac tgcagcctga ggatgtggca gcttattatt gccagcagtc tatcaagctg   1080
ccattcacct ttggttccgg cacaaaagtc gaaattaagg aggaggtgg aagcggagga   1140 ggtggatctg gaggaggtgg aagtgaggtg cagctggtcg aaagcggagc aggggtgaaa   1200
cagccaggag ggacactgag gctgacttgt accgccagcg gattctctct gacaacttac   1260
ggagtgcact gggtccgaca ggcaccaggc aagggactgg agtgggtggg agtcatctgg   1320
ggagatgggc gcaccgacta cgatgctgca tttatgtcac gagtgacaat ttctaaagac   1380
acatccaaga gcactgtcta tctgcagatg aactctctgc gcgcagagga tactgccgtg   1440
```

```
tactattgca tgaggaatcg gcatgactgg tttgattact ggggtcaggg caccacagtg   1500
accgtctcca gccaccatca ccatcaccat tgataa                              1536
```

<210> SEQ ID NO 24
<211> LENGTH: 6
<212> TYPE: DNA
<213> ORGANISM: Anabaena variabilis

<400> SEQUENCE: 24 cctagg                                                                  6

<210> SEQ ID NO 25
<211> LENGTH: 6
<212> TYPE: DNA
<213> ORGANISM: Artificial Sequence
<220> FEATURE:
<223> OTHER INFORMATION: Synthetic: eukaryotes

<400> SEQUENCE: 25 gccacc                                                                  6

<210> SEQ ID NO 26
<211> LENGTH: 6
<212> TYPE: DNA
<213> ORGANISM: Bacillus stearothermophilus

<400> SEQUENCE: 26 gtatac                                                                  6

<210> SEQ ID NO 27
<211> LENGTH: 18
<212> TYPE: DNA
<213> ORGANISM: Artificial Sequence
<220> FEATURE:
<223> OTHER INFORMATION: Synthetic: primer

<400> SEQUENCE: 27
tgtaaaacga cggccagt                                                    18

<210> SEQ ID NO 28
<211> LENGTH: 17
<212> TYPE: DNA
<213> ORGANISM: Artificial Sequence
<220> FEATURE:
<223> OTHER INFORMATION: Synthetic: primer

<400> SEQUENCE: 28
caggaaacag ctatgac                                                     17

<210> SEQ ID NO 29
<211> LENGTH: 238
<212> TYPE: PRT
<213> ORGANISM: Homo sapiens

<400> SEQUENCE: 29

Glu Val Gln Leu Val Glu Ser Gly Ala Gly Val Lys Gln Pro Gly Gly
 1               5                  10                  15

Thr Leu Arg Leu Thr Cys Thr Ala Ser Gly Phe Ser Leu Thr Thr Tyr
            20                  25                  30

Gly Val His Trp Val Arg Gln Ala Pro Gly Lys Gly Leu Glu Trp Val
        35                  40                  45

Gly Val Ile Trp Gly Asp Gly Arg Thr Asp Tyr Asp Ala Ala Phe Met
    50                  55                  60

```
Ser Arg Val Thr Ile Ser Lys Asp Thr Ser Lys Ser Thr Val Tyr Leu
 65                  70                  75                  80

Gln Met Asn Ser Leu Arg Ala Glu Asp Thr Ala Val Tyr Tyr Cys Met
                 85                  90                  95

Arg Asn Arg His Asp Trp Phe Asp Tyr Trp Gly Gln Gly Thr Thr Val
            100                 105                 110

Thr Val Ser Ser Gly Gly Gly Gly Ser Gly Gly Gly Gly Ser Gly Gly
        115                 120                 125

Gly Gly Ser Asp Ile Leu Leu Thr Gln Ser Pro Ser Ser Leu Ser Ala
    130                 135                 140

Thr Pro Gly Glu Arg Ala Thr Ile Thr Cys Arg Ala Ser Gln Gly Ile
145                 150                 155                 160

Arg Asn Asn Leu Asn Trp Tyr Gln Gln Lys Pro Gly Gln Ala Pro Arg
                165                 170                 175

Leu Leu Ile Tyr Tyr Ser Ser Asn Leu Gln Ser Gly Val Pro Ser Arg
            180                 185                 190

Phe Ser Gly Ser Gly Ser Gly Thr Asp Phe Thr Leu Thr Ile Ser Arg
        195                 200                 205

Leu Gln Pro Glu Asp Val Ala Ala Tyr Tyr Cys Gln Gln Ser Ile Lys
    210                 215                 220

Leu Pro Phe Thr Phe Gly Ser Gly Thr Lys Val Glu Ile Lys
225                 230                 235

<210> SEQ ID NO 30
<211> LENGTH: 243
<212> TYPE: PRT
<213> ORGANISM: Homo sapiens

<400> SEQUENCE: 30

Asp Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Ile
            35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
 65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
```

```
                195                 200                 205
Leu Thr Ile Asn Ser Leu Glu Ala Glu Asp Ala Ala Thr Tyr Tyr Cys
        210                 215                 220

Gln Gln Trp Ser Ser Asn Pro Leu Thr Phe Gly Gly Gly Thr Lys Val
225                 230                 235                 240

Glu Ile Lys

<210> SEQ ID NO 31
<211> LENGTH: 738
<212> TYPE: DNA
<213> ORGANISM: Homo sapiens

<400> SEQUENCE: 31
gaagttcaac tggtggaatc tggcgctggt gtcaaacaac cggqtggcac gctgcgtctg      60 acctgcacgg caagtggctt ttctctgacc acgtatggtg ttcattgggt ccgtcaggca     120
ccgggtaaag gtctggaatg ggtgggcgtt atttggggcg atggtcgcac cgattatgac     180
gcggccttta tgtctcgtgt gacgatcagt aaagatacca gcaagtctac ggtttacctg     240
cagatgaaca gtctgcgcgc ggaagacacc gccgtgtatt actgcatgcg taatcgccac     300
gattggttcg actattgggg ccaaggtacc acggtcaccg tgagctctgg cggtggcggt     360
tccggcggtg gcggttcagg cggtggcggt tcggatattc tgctgaccca gagcccgagt     420
tccctgtctg caacgccggg tgaacgtgct accattacgt gtcgcgcgag ccaaggcatc     480
cgtaacaatc tgaactggta ccagcaaaag ccgggtcagg caccgcgtct gctgatttat     540
tactcatcga atctgcaatc gggcgtcccg agccgtttta gtggctccgg ttcaggcacc     600
gatttcaccc tgacgatcag ccgcctgcag ccggaagacg ttgcagctta ttactgtcaa     660 cagagccatca aactgccgtt caccttcggt tcaggcacca agtggaaat caagcatcat     720 catcaccatc actagtaa                                                   738

<210> SEQ ID NO 32
<211> LENGTH: 753
<212> TYPE: DNA
<213> ORGANISM: Homo sapiens

<400> SEQUENCE: 32
gacgtgcagc tggtccagag cggagcagaa gtcaagaaac caggggcctc cgtgaaagtc      60
agctgtaagg catctggcta cacttttacc aggtacacca tgcactgggt cagacaggca     120
ccaggacagg gactggagtg gatcggttac attaacccct ctcggggta caccaattat     180 gctgactccg tgaaaggcag attcacaatc acaactgata gtctacaag tactgcatat     240 atggagctga ctctctgcg ttctgaagac accgcaacat actattgcgc caggtactat     300
gacgatcatt actgtctgga ttattggggg cagggtacca cagtgaccgt cagttcaggc     360
gagggaactt caaccggatc cggaggtagc ggaggatctg gaggtgctga cgatattgtg     420
ctgactcaga gcccagcaac cctgtcactg tcccctggag aacgtgccac actgtcttgc     480
agggctagcc agtctgtgag ttacatgaac tggtatcagc agaagccagg aaaagctccc     540
aagaggtgga tctacgatac tagtaaggtg gcttcaggcg tcccagcacg atttcaggg     600 tccggtagcg gcacagacta ttcactgact attaactctc tggaggccga agatgctgca     660
acctactatt gtcagcagtg gtccagcaat ccctgacct tcggcggagg gacaaaagtg     720
gagatcaagc accatcacca tcaccattga taa                                  753
```

<210> SEQ ID NO 33
<211> LENGTH: 738
<212> TYPE: DNA
<213> ORGANISM: Homo sapiens

<400> SEQUENCE: 33

| | | | | | | |
|---|---|---|---|---|---|---|
| gaagttcaat | tggtcgaatc | tggtgctgga | gttaagcagc | caggtggaac | tttgagactt | 60 |
| acctgtacag | ccagtggatt | ttctttgact | acctacggtg | ttcattgggt | cagacaagct | 120 |
| ccaggtaaag | gtttgaatg | ggttggtgtc | atttggggag | atggaagaac | cgattacgac | 180 |
| gctgccttca | tgagtagagt | tacaatctct | aaggatacct | caaaaagtac | agtctatttg | 240 |
| caaatgaact | ctcttagagc | cgaggacact | gcagtttact | actgtatgag | aaacagacac | 300 |
| gattggtttg | actactgggg | tcagggaaca | actgttaccg | tctcttccgg | tggaggtgga | 360 |
| tccggtggag | gtggatctgg | tggaggtgga | agtgacattt | tgcttacaca | atctccatca | 420 |
| agtttgtccg | ctactcctgg | agaaagagcc | actattacct | gcagagcatc | tcagggtatc | 480 |
| agaaacaatt | tgaactggta | tcaacagaag | ccaggtcaag | ctcctagatt | gcttatctac | 540 |
| tattcttcca | atttgcagtc | cggtgttcca | tcaagatttt | ctggttccgg | atcaggtact | 600 |
| gatttcacat | tgactatctc | cagacttcaa | ccagaagacg | ttgcagctta | ctattgccaa | 660 |
| cagtcaatta | aattgccttt | tactttcgga | agtggtacta | aggtcgagat | caaacatcac | 720 |
| catcaccatc | actaatag | | | | | 738 |

<210> SEQ ID NO 34
<211> LENGTH: 753
<212> TYPE: DNA
<213> ORGANISM: Homo sapiens

<400> SEQUENCE: 34

| | | | | | | |
|---|---|---|---|---|---|---|
| gatgttcagt | tggtccagtc | cggtgctgag | gtcaaaaagc | caggagccag | tgtcaaagtt | 60 |
| agttgtaaag | ccagtggtta | taccttcact | agatatacaa | tgcattgggt | cagacaagca | 120 |
| ccaggacaag | gattggaatg | gatcggttac | attaatccat | ccagaggata | taccaattac | 180 |
| gctgacagtg | tcaaaggtag | attcactatt | actacagaca | agagtacttc | tacagcctac | 240 |
| atggaattgt | cctctcttag | atcagaagac | accgctactt | attactgtgc | tagatactac | 300 |
| gatgatcatt | attgtcttga | ttactggggt | caaggaacca | ctgttactgt | ctcctctgga | 360 |
| gaaggtactt | caaccggtag | tggaggttca | ggtggatcag | gaggtgctga | cgatattgtt | 420 |
| ttgacccaat | ctccagcaac | attgtcccct | agtcctggag | agagagccac | acttagttgt | 480 |
| agagcttccc | aatcagtctc | ctacatgaac | tggtatcagc | aaaagcctgg | taagctcca | 540 |
| aaaagatgga | tctacgacac | ctcaaaagtc | gcctcaggtg | ttcctgctag | attttctgga | 600 |
| agtggtcag | gtactgatta | ctcacttact | atcaactctt | tggaggctga | agacgcagcc | 660 |
| acttactatt | gtcagcaatg | gtcaagtaat | ccattgacat | tcggaggagg | aacaaaggtt | 720 |
| gagattaagc | atcatcatca | tcaccattag | taa | | | 753 |

<210> SEQ ID NO 35
<211> LENGTH: 6
<212> TYPE: DNA
<213> ORGANISM: Xanthomonas holcicola

<400> SEQUENCE: 35

| | |
|---|---|
| ctcgag | 6 |

<210> SEQ ID NO 36

```
<211> LENGTH: 6
<212> TYPE: DNA
<213> ORGANISM: Xanthomonas badrii

<400> SEQUENCE: 36 tctaga                                                                      6

<210> SEQ ID NO 37
<211> LENGTH: 446
<212> TYPE: PRT
<213> ORGANISM: Homo sapiens

<400> SEQUENCE: 37
```

| | | | | | | | | | | | | | | | |
|---|---|---|---|---|---|---|---|---|---|---|---|---|---|---|---|
| Glu | Val | Gln | Leu | Val | Glu | Ser | Gly | Ala | Gly | Val | Lys | Gln | Pro | Gly | Gly |
| 1 | | | | 5 | | | | | 10 | | | | | 15 | |
| Thr | Leu | Arg | Leu | Thr | Cys | Thr | Ala | Ser | Gly | Phe | Ser | Leu | Thr | Thr | Tyr |
| | | | 20 | | | | | 25 | | | | | 30 | | |
| Gly | Val | His | Trp | Val | Arg | Gln | Ala | Pro | Gly | Lys | Gly | Leu | Glu | Trp | Val |
| | | | 35 | | | | | 40 | | | | | 45 | | |
| Gly | Val | Ile | Trp | Gly | Asp | Gly | Arg | Thr | Asp | Tyr | Asp | Ala | Ala | Phe | Met |
| 50 | | | | | 55 | | | | | 60 | | | | | |
| Ser | Arg | Val | Thr | Ile | Ser | Lys | Asp | Thr | Ser | Lys | Ser | Thr | Val | Tyr | Leu |
| 65 | | | | | 70 | | | | | 75 | | | | | 80 |
| Gln | Met | Asn | Ser | Leu | Arg | Ala | Glu | Asp | Thr | Ala | Val | Tyr | Tyr | Cys | Met |
| | | | | 85 | | | | | 90 | | | | | 95 | |
| Arg | Asn | Arg | His | Asp | Trp | Phe | Asp | Tyr | Trp | Gly | Gln | Gly | Thr | Thr | Val |
| | | | 100 | | | | | 105 | | | | | 110 | | |
| Thr | Val | Ser | Ser | Ala | Ser | Thr | Lys | Gly | Pro | Ser | Val | Phe | Pro | Leu | Ala |
| | | | 115 | | | | | 120 | | | | | 125 | | |
| Pro | Ser | Ser | Lys | Ser | Thr | Ser | Gly | Gly | Thr | Ala | Ala | Leu | Gly | Cys | Leu |
| 130 | | | | | 135 | | | | | 140 | | | | | |
| Val | Lys | Asp | Tyr | Phe | Pro | Glu | Pro | Val | Thr | Val | Ser | Trp | Asn | Ser | Gly |
| 145 | | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 | |
| Gly | Leu | Tyr | Ser | Leu | Ser | Ser | Val | Val | Thr | Val | Pro | Ser | Ser | Ser | Leu |
| | | | 180 | | | | | 185 | | | | | 190 | | |
| Gly | Thr | Gln | Thr | Tyr | Ile | Cys | Asn | Val | Asn | His | Lys | Pro | Ser | Asn | Thr |
| | | | 195 | | | | | 200 | | | | | 205 | | |
| Lys | Val | Asp | Lys | Lys | Val | Glu | Pro | Lys | Ser | Cys | Asp | Lys | Thr | His | Thr |
| 210 | | | | | 215 | | | | | 220 | | | | | |
| Cys | Pro | Pro | Cys | Pro | Ala | Pro | Glu | Leu | Leu | Gly | Gly | Pro | Ser | Val | Phe |
| 225 | | | | | 230 | | | | | 235 | | | | | 240 |
| Leu | Phe | Pro | Pro | Lys | Pro | Lys | Asp | Thr | Leu | Met | Ile | Ser | Arg | Thr | Pro |
| | | | | 245 | | | | | 250 | | | | | 255 | |
| Glu | Val | Thr | Cys | Val | Val | Val | Asp | Val | Ser | His | Glu | Asp | Pro | Glu | Val |
| | | | 260 | | | | | 265 | | | | | 270 | | |
| Lys | Phe | Asn | Trp | Tyr | Val | Asp | Gly | Val | Glu | Val | His | Asn | Ala | Lys | Thr |
| | | | 275 | | | | | 280 | | | | | 285 | | |
| Lys | Pro | Arg | Glu | Glu | Gln | Tyr | Asn | Ser | Thr | Tyr | Arg | Val | Val | Ser | Val |
| | | | 290 | | | | | 295 | | | | | 300 | | |
| Leu | Thr | Val | Leu | His | Gln | Asp | Trp | Leu | Asn | Gly | Lys | Glu | Tyr | Lys | Cys |
| 305 | | | | | 310 | | | | | 315 | | | | | 320 |
| Lys | Val | Ser | Asn | Lys | Ala | Leu | Pro | Ala | Pro | Ile | Glu | Lys | Thr | Ile | Ser |
| | | | | 325 | | | | | 330 | | | | | 335 | |

```
Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Ile Thr Val Asp Lys Ser Arg Trp
                405                 410                 415

Gln Gln Gly Asn Val Phe Ser Gly Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 38
<211> LENGTH: 214
<212> TYPE: PRT
<213> ORGANISM: Homo sapiens

<400> SEQUENCE: 38

Asp Ile Leu Leu Thr Gln Ser Pro Ser Ser Leu Ser Ala Thr Pro Gly
1               5                   10                  15

Glu Arg Ala Thr Ile Thr Cys Arg Ala Ser Gln Gly Ile Arg Asn Asn
            20                  25                  30

Leu Asn Trp Tyr Gln Gln Lys Pro Gly Gln Ala Pro Arg Leu Leu Ile
        35                  40                  45

Tyr Tyr Ser Ser Asn Leu Gln Ser Gly Val Pro Ser Arg Phe Ser Gly
    50                  55                  60

Ser Gly Ser Gly Thr Asp Phe Thr Leu Thr Ile Ser Arg Leu Gln Pro
65                  70                  75                  80

Glu Asp Val Ala Ala Tyr Tyr Cys Gln Gln Ser Ile Lys Leu Pro Phe
                85                  90                  95

Thr Phe Gly Ser Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 39
<211> LENGTH: 20
<212> TYPE: PRT
<213> ORGANISM: Mus musculus

<400> SEQUENCE: 39
```

```
Met Glu Thr Asp Thr Leu Leu Leu Trp Val Leu Leu Leu Trp Val Pro
1               5                   10                  15

Gly Ser Thr Gly
            20
```

<210> SEQ ID NO 40
<211> LENGTH: 1401
<212> TYPE: DNA
<213> ORGANISM: Homo sapiens

<400> SEQUENCE: 40

| | |
|---|---:|
| atggagacag acacactcct gctatgggtg ctgctgctct gggttccagg ttccactggt | 60 |
| gaagttcaat tagtcgagtc tggtgctggc gtaaaacagc tggagggac tttgcgtctt | 120 |
| acctgtacag cctccggttt ttcactcacg acttatggcg tgcattgggt tcgccaagca | 180 |
| cccggaaagg ggctagaatg ggtcggtgta atttggggcg atggacgaac cgactacgat | 240 |
| gcggctttca tgtcgcgggt gacaatcagt aaagacacga gcaagtctac tgtttatctg | 300 |
| cagatgaatt ccttaagagc cgaggatacc gcagtctact attgcatgag gaaccgtcac | 360 |
| gactggtttg attactgggg gcaaggtaca acggtaactg tgtcatcggc gagtaccaaa | 420 |
| ggcccaagcg ttttcccgtt ggctccttct tccaagtcaa catcgggagg acggccgca | 480 |
| cttggttgtc tcgtcaaaga ctattttccc gaaccagtaa ctgtgagttg aatagcggc | 540 |
| gcgctaacct ctggagttca tacattcccg gctgtcctgc agtcctcagg ttatactcg | 600 |
| ttgagtagcg tagtgacggt tccttcttcc tcacttggta ctcaaaccta tatgcaac | 660 |
| gtcaatcaca agccctcgaa cacaaaagta gataagaaag tggagccaaa gagttgtgac | 720 |
| aaaacgcata cttgcccgcc ttgtcccgcc ccagaactcc taggcggacc gagcgttttt | 780 |
| ctgttccctc ccaagccaaa agataccta atgatttctc gcacaccgga ggtcacgtgc | 840 |
| gtagtggttg acgtctccca cgaagatcct gaggtaaagt ttaattggta cgtggacggg | 900 |
| gttgaagtcc ataacgcaaa aactaagccc cgagaggaac agtataattc aacctaccgg | 960 |
| gtagtgtcgg ttttgacagt ccttcaccaa gattggctca acggtaaaga gtataagtgt | 1020 |
| aaagtaagta ataaggcgct accagctccg atcgaaaaaa cgataagcaa ggccaaaggc | 1080 |
| cagcctagag agccccaagt gtacactctg ccaccgtcta gggacgaatt aaccaagaac | 1140 |
| caggtttcct tgacatgcct tgtcaaagga ttctatcctt cagatattgc agtagagtgg | 1200 |
| gaatcgaatg ggcaacccga gaacaattac aagacgactc caccggtgct cgacagtgat | 1260 |
| ggtagctttt tcctatattc taaaatcacc gttgacaagt cccgttggca gcaaggcaac | 1320 |
| gtcttttcag gatcggtaat gcatgaagcg ctgcacaatc attacacaca gaaaagttta | 1380 |
| agcttgtctc ctgggaagta a | 1401 |

<210> SEQ ID NO 41
<211> LENGTH: 705
<212> TYPE: DNA
<213> ORGANISM: Homo sapiens

<400> SEQUENCE: 41

| | |
|---|---:|
| atggagacag acacactcct gctatgggtg ctgctgctct gggttccagg ttccactggt | 60 |
| gatatttat tgactcaatc tccttcctca ctttcggcta ccccggtga acgtgccaca | 120 |
| atcacgtgtc gcgcaagtca gggcatacga ataaacctca attggtatca acagaaacca | 180 |
| ggacaagcgc cgcggctact gatttactat agctctaact acagtccggg gttccttca | 240 |
| agattttcgg gtagtggcag cggaactgac ttcacccttga caatctctag gcttcaaccc | 300 |

```
gaggatgtcg ctgcctacta ttgccagcaa tccataaagc tcccatttac gttcgggtca    360
ggtactaaag tagaaattaa gcgtaccgtg gcagcgccgt cggttttat cttccctccc     420 agtgacgagc agctaaaaag cggcacagct tctgtcgtat gtctgttaaa taacttttac    480
ccacgcgaag ccaaggtgca atggaaagtt gataatgcat tgcagtccgg aaactcacaa    540
gagtcggtca cggaacagga cagtaaggat agcacttatt ctctttcctc aaccctcaca    600
ctatcgaaag cggactacga gaagcataaa gtatatgctt gcgaagtgac gcaccaaggg    660
ctgagtagcc cggttactaa gtctttcaat cgaggtgagt gttaa                   705
```

<210> SEQ ID NO 42
<211> LENGTH: 1401
<212> TYPE: DNA
<213> ORGANISM: Homo sapiens

<400> SEQUENCE: 42

```
atggagacag acacactcct gctatgggta ctgctgctct ggttccagg ttccactggt      60 gaggtccagc tggtcgagag cggcgcaggg gtcaagcagc ccggcggaac actgagactg    120
acatgcacag caagcggttt ttcactgacc acatacggag tccactgggt gagacaggca    180
cctggcaagg gactggaatg ggtcggagtg atctggggg acggtcgaac cgactacgat    240
gccgctttca tgagccgtgt cacaatttct aaggacacaa gcaaatctac cgtgtacctg    300
cagatgaaca gcctgcgcgc cgaggatacc gccgtgtact attgcatgag gaatcggcat    360
gactggttcg attactgggg ccagggaact accgtcaccg tgtcctccgc cagtacaaag    420
ggcccatcag tgtttccact ggcaccctct agtaaaagta cctcaggcgg aacagcagcc    480 ctggatgtc tggtgaagga ttatttccca gagcccgtca ccgtgtcttg aacagtggg     540 gcactgacat ccggtgtcca cttttttcca gccgtgctgc agtcatccgg ctgtactcc     600 ctgagctctg tggtcacagt gcccagttca tccctgggta cccagacata tatctgcaac    660
gtgaatcaca agccaagtaa tactaaagtc gacaagaaag tggaacccaa gtcttgtgat    720
aaaactcata cctgccccc ttgtcctgca ccagagctgc tgggaggtcc atccgtgttc    780
ctgtttccac ccaagcctaa agacaccctg atgatttccc gaactcccga agtcacctgc    840
gtggtcgtgg acgtgtccca cgaggatcct gaagtcaagt ttaactggta cgtggatggc    900
gtcgaggtgc ataatgctaa gacaaaaccc agagaggaac agtacaactc cacatatcgc    960
gtcgtgagcg tcctgactgt gctgcatcag gactggctga acgggaagga atataagtgc    1020
aaagtgagca ataaggctct gcccgcacct atcgagaaaa ctatttctaa ggccaaaggc    1080
cagcctaggg aaccacaggt gtacaccctg cctccaagcc gggacgagct gactaagaac    1140
caggtctctc tgacctgtct ggtgaaaggg ttctatcctt cagatatcgc tgtggagtgg    1200
gaatccaatg gtcagccaga gaacaattac aagacaactc cccctgtgct ggactcagat    1260
ggatccttct ttctgtattc taagattacc gtggataaaa gtcggtggca gcagggcaat    1320
gtcttttccg gaagcgtgat gcacgaagca ctgcacaatc actacactca gaagtccctg    1380
tccctgtcac ctggtaaatg a                                             1401
```

<210> SEQ ID NO 43
<211> LENGTH: 705
<212> TYPE: DNA
<213> ORGANISM: Homo sapiens

<400> SEQUENCE: 43

```
atggagacag acacactcct gctatgggta ctgctgctct gggttccagg ttccactggt    60
gacattctgc tgacccagag cccaagttca ctgagcgcaa caccaggcga gcgtgctacc   120
attacatgcc gtgcttccca ggggattagg aacaatctga actggtacca gcagaagcca   180
ggacaggcac cccggctgct gatctactat tccagcaatc tgcagagtgg ggtgccatca   240
agattctcag gctccggaag cgggacagac tttaccctga caatcagccg actgcagcct   300
gaggatgtgg cagcttacta ttgccagcag tccattaagc tgccattcac atttggttcc   360
ggcactaagg tcgagatcaa acgaactgtg gcagccccct ctgtcttcat ttttcccct    420 agtgacgaac agctgaaatc cggaaccgct agcgtggtct gtctgctgaa caatttctac   480
cctagggagg ctaaggtgca gtggaaagtc gataacgcac tgcagtctgg caatagtcag   540
gagtcagtga ccgaacagga ctccaaggat agcacatatt ctctgtctag tactctgacc   600
ctgtctaaag ccgactacga aaagcacaaa gtgtatgctt gcgaggtcac ccatcagggg   660
ctgtcatcac cagtcaccaa gtccttcaat cgtggcgagt gctga                    705

<210> SEQ ID NO 44
<211> LENGTH: 6
<212> TYPE: DNA
<213> ORGANISM: E. coli

<400> SEQUENCE: 44 gatatc                                                                6

<210> SEQ ID NO 45
<211> LENGTH: 8
<212> TYPE: DNA
<213> ORGANISM: Pseudomonas alcaligenes

<400> SEQUENCE: 45 ttaattaa                                                              8
```